(12) United States Patent
Gross et al.

(10) Patent No.: US 10,226,341 B2
(45) Date of Patent: *Mar. 12, 2019

(54) IMPLANT FOR HEART VALVE

(71) Applicant: CARDIOVALVE LTD., Or Yehuda (IL)

(72) Inventors: Yossi Gross, Moshav Mazor (IL); Gil Hacohen, Ramat Gan (IL); Eran Miller, Moshav Beit Elazari (IL); Yuval Zipory, Modi'in (IL); Tal Reich, Moshav Moledet (IL); Meir Kutzik, Holon (IL); Rotem Neeman, Yeshuv Nirit (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/197,069

(22) Filed: Jun. 29, 2016

(65) Prior Publication Data

US 2016/0310274 A1    Oct. 27, 2016

Related U.S. Application Data

(63) Continuation of application No. 14/237,258, filed as application No. PCT/IL2012/000293 on Aug. 5, (Continued)

(51) Int. Cl.
*A61F 2/24* (2006.01)
*A61F 2/848* (2013.01)

(52) U.S. Cl.
CPC .......... *A61F 2/2442* (2013.01); *A61F 2/2409* (2013.01); *A61F 2/2418* (2013.01);
(Continued)

(58) Field of Classification Search
CPC ......... A61F 2/24; A61F 2/2436; A61F 2/2418
(Continued)

(56) References Cited

U.S. PATENT DOCUMENTS

| 4,261,342 A | 4/1981 | Aranguren Duo |
| 4,423,525 A | 1/1984 | Vallana et al. |

(Continued)

FOREIGN PATENT DOCUMENTS

| EP | 1264582 A2 | 12/2002 |
| EP | 1768630 B1 | 4/2007 |

(Continued)

OTHER PUBLICATIONS

Extended European Search Report dated Jun. 29, 2017; Appln. No. 11809374.9.

(Continued)

*Primary Examiner* — Suzette J Gherbi
(74) *Attorney, Agent, or Firm* — Ladas & Parry LLP

(57) ABSTRACT

For some applications, apparatus is provided for facilitating implantation of a prosthetic valve at a native heart valve of a subject, the apparatus comprising a prosthetic valve support, the prosthetic valve support (a) being configured to be transluminally-deliverable to the native valve and to be deployable at the native valve, and (b) comprising one or more tissue-engaging elements, configured to couple the prosthetic valve support to leaflets of the native valve without eliminating check valve functionality of the native valve. Other embodiments are also described.

21 Claims, 13 Drawing Sheets

Related U.S. Application Data 2012, now Pat. No. 9,387,078, which is a continuation-in-part of application No. 13/412,814, filed on Mar. 6, 2012, now Pat. No. 8,852,272.

(60) Provisional application No. 61/588,892, filed on Jan. 20, 2012, provisional application No. 61/555,160, filed on Nov. 3, 2011, provisional application No. 61/537,276, filed on Sep. 21, 2011, provisional application No. 61/525,281, filed on Aug. 19, 2011, provisional application No. 61/515,372, filed on Aug. 5, 2011.

(52) U.S. Cl.
CPC .......... *A61F 2/2436* (2013.01); *A61F 2/2439* (2013.01); *A61F 2/2454* (2013.01); *A61F 2/2466* (2013.01); *A61F 2/2445* (2013.01); *A61F 2/848* (2013.01); *A61F 2220/0016* (2013.01); *A61F 2220/0025* (2013.01); *A61F 2220/0091* (2013.01); *A61F 2230/0006* (2013.01); *A61F 2230/0013* (2013.01); *A61F 2250/006* (2013.01); *A61F 2250/0015* (2013.01); *A61F 2250/0069* (2013.01); *A61F 2250/0071* (2013.01)

(58) Field of Classification Search
USPC .................................................. 623/2.1–1.19
See application file for complete search history.

(56) References Cited

U.S. PATENT DOCUMENTS

| | | |
|---|---|---|
| 4,853,986 A | 8/1989 | Allen |
| 4,892,541 A | 1/1990 | Alonso |
| 5,108,420 A | 4/1992 | Marks |
| 5,314,473 A | 5/1994 | Godin |
| 5,405,378 A | 4/1995 | Strecker |
| 5,443,500 A | 8/1995 | Sigwart |
| 5,607,444 A | 3/1997 | Lam |
| 5,607,470 A | 3/1997 | Milo |
| 5,647,857 A | 7/1997 | Anderson et al. |
| 5,765,682 A | 6/1998 | Bley et al. |
| 5,868,777 A | 2/1999 | Lam |
| 5,873,906 A | 2/1999 | Lau et al. |
| 5,954,766 A | 9/1999 | Zadno-Azizi et al. |
| 5,980,565 A | 11/1999 | Jayaraman |
| 6,019,787 A | 2/2000 | Richard et al. |
| 6,042,607 A | 3/2000 | Williamson, IV et al. |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vazquez et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,733,525 B2 | 5/2004 | Yang et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,893,460 B2 | 5/2005 | Spenser et al. |
| 6,960,217 B2 | 11/2005 | Bolduc |
| 6,964,684 B2 | 11/2005 | Ortiz et al. |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,137,184 B2 | 11/2006 | Schreck |
| 7,172,625 B2 | 2/2007 | Shu et al. |
| 7,198,646 B2 | 4/2007 | Figulla et al. |
| 7,201,772 B2 | 4/2007 | Schwammenthal et al. |
| 7,226,477 B2 | 6/2007 | Cox |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,556,646 B2 | 7/2009 | Yang et al. |
| 7,582,111 B2 | 9/2009 | Krolik et al. |
| 7,585,321 B2 | 9/2009 | Cribier |
| 7,597,711 B2 | 10/2009 | Drews et al. |
| 7,611,534 B2 | 11/2009 | Kapadia et al. |
| 7,621,948 B2 | 11/2009 | Herrmann et al. |
| 7,625,403 B2 | 12/2009 | Krivoruchko |
| 7,632,302 B2 | 12/2009 | Vreeman et al. |
| 7,648,528 B2 | 1/2010 | Styrc |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |

(56) References Cited

U.S. PATENT DOCUMENTS

| | | | |
|---|---|---|---|
| 7,799,069 | B2 | 9/2010 | Bailey et al. |
| 7,803,181 | B2 | 9/2010 | Furst et al. |
| 7,811,316 | B2 | 10/2010 | Kalmann et al. |
| 7,824,442 | B2 | 11/2010 | Salahieh et al. |
| 7,837,645 | B2 | 11/2010 | Bessler et al. |
| 7,837,727 | B2 | 11/2010 | Goetz et al. |
| 7,842,081 | B2 | 11/2010 | Yadin |
| 7,850,725 | B2 | 12/2010 | Vardi et al. |
| 7,871,432 | B2 | 1/2011 | Bergin |
| 7,871,436 | B2 | 1/2011 | Ryan et al. |
| 7,887,583 | B2 | 2/2011 | Macoviak |
| 7,892,281 | B2 | 2/2011 | Seguin et al. |
| 7,896,915 | B2 | 3/2011 | Guyenot et al. |
| 7,914,544 | B2 | 3/2011 | Nguyen et al. |
| 7,914,569 | B2 | 3/2011 | Nguyen et al. |
| 7,927,370 | B2 | 4/2011 | Webler et al. |
| 7,942,927 | B2 | 5/2011 | Kaye et al. |
| 7,947,072 | B2 | 5/2011 | Yang et al. |
| 7,947,075 | B2 | 5/2011 | Goetz et al. |
| 7,955,375 | B2 | 6/2011 | Agnew |
| 7,955,377 | B2 | 6/2011 | Melsheimer |
| 7,955,384 | B2 | 6/2011 | Rafiee et al. |
| 7,959,666 | B2 | 6/2011 | Salahieh et al. |
| 7,959,672 | B2 | 6/2011 | Salahieh et al. |
| 7,967,833 | B2 | 6/2011 | Sterman et al. |
| 7,967,857 | B2 | 6/2011 | Lane |
| 7,981,151 | B2 | 7/2011 | Rowe |
| 7,981,153 | B2 | 7/2011 | Fogarty et al. |
| 7,992,567 | B2 | 8/2011 | Hirotsuka et al. |
| 7,993,393 | B2 | 8/2011 | Carpentier et al. |
| 8,002,825 | B2 | 8/2011 | Letac et al. |
| 8,002,826 | B2 | 8/2011 | Seguin |
| 8,016,877 | B2 | 9/2011 | Seguin et al. |
| 8,016,882 | B2 | 9/2011 | Macoviak et al. |
| 8,021,420 | B2 | 9/2011 | Dolan |
| 8,021,421 | B2 | 9/2011 | Fogarty et al. |
| 8,025,695 | B2 | 9/2011 | Fogarty et al. |
| 8,029,518 | B2 | 10/2011 | Goldfarb et al. |
| 8,029,557 | B2 | 10/2011 | Sobino-Serrano et al. |
| 8,029,564 | B2 | 10/2011 | Johnson et al. |
| 8,034,104 | B2 | 10/2011 | Carpentier et al. |
| 8,038,720 | B2 | 10/2011 | Wallace et al. |
| 8,043,360 | B2 | 10/2011 | McNamara et al. |
| 8,048,138 | B2 | 11/2011 | Sullivan et al. |
| 8,048,140 | B2 | 11/2011 | Purdy |
| 8,048,153 | B2 | 11/2011 | Salahieh et al. |
| 8,052,741 | B2 | 11/2011 | Bruszewski et al. |
| 8,052,749 | B2 | 11/2011 | Salahieh et al. |
| 8,057,493 | B2 | 11/2011 | Goldfarb et al. |
| 8,057,532 | B2 | 11/2011 | Hoffman |
| 8,057,540 | B2 | 11/2011 | Letac et al. |
| 8,062,355 | B2 | 11/2011 | Figulla et al. |
| 8,062,359 | B2 | 11/2011 | Marquez et al. |
| 8,070,708 | B2 | 12/2011 | Rottenberg et al. |
| 8,070,800 | B2 | 12/2011 | Lock et al. |
| 8,070,802 | B2 | 12/2011 | Lamphere et al. |
| 8,070,804 | B2 | 12/2011 | Hyde et al. |
| 8,075,611 | B2 | 12/2011 | Millwee et al. |
| 8,080,054 | B2 | 12/2011 | Rowe |
| 8,083,793 | B2 | 12/2011 | Lane et al. |
| D652,927 | S | 1/2012 | Braido et al. |
| D653,341 | S | 1/2012 | Braido et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,105,377 | B2 | 1/2012 | Liddicoat |
| 8,109,996 | B2 | 2/2012 | Stacchino et al. |
| 8,118,866 | B2 | 2/2012 | Herrmann et al. |
| 8,133,270 | B2 | 3/2012 | Kheradvar et al. |
| 8,136,218 | B2 | 3/2012 | Millwee et al. |
| 8,137,398 | B2 | 3/2012 | Tuval et al. |
| 8,142,492 | B2 | 3/2012 | Forster et al. |
| 8,142,494 | B2 | 3/2012 | Rahdert et al. |
| 8,142,496 | B2 | 3/2012 | Berreklouw |
| 8,142,497 | B2 | 3/2012 | Friedman |
| 8,147,504 | B2 | 4/2012 | Ino et al. |
| 8,157,852 | B2 | 4/2012 | Bloom et al. |
| 8,157,853 | B2 | 4/2012 | Laske et al. |
| 8,157,860 | B2 | 4/2012 | McNamara et al. |
| 8,163,008 | B2 | 4/2012 | Wilson et al. |
| 8,163,014 | B2 | 4/2012 | Lane et al. |
| D660,433 | S | 5/2012 | Braido et al. |
| D660,967 | S | 5/2012 | Braido et al. |
| 8,167,894 | B2 | 5/2012 | Miles et al. |
| 8,167,932 | B2 | 5/2012 | Bourang et al. |
| 8,167,935 | B2 | 5/2012 | McGuckin, Jr. et al. |
| 8,172,896 | B2 | 5/2012 | McNamara et al. |
| 8,172,898 | B2 | 5/2012 | Alferness et al. |
| 8,177,836 | B2 | 5/2012 | Lee et al. |
| 8,182,528 | B2 | 5/2012 | Salahieh et al. |
| 8,211,169 | B2 | 7/2012 | Lane et al. |
| 8,216,301 | B2 | 7/2012 | Bonhoeffer et al. |
| 8,221,492 | B2 | 7/2012 | Case et al. |
| 8,221,493 | B2 | 7/2012 | Boyle et al. |
| 8,226,710 | B2 | 7/2012 | Nguyen et al. |
| 8,231,670 | B2 | 7/2012 | Salahieh et al. |
| 8,236,045 | B2 | 8/2012 | Benichou et al. |
| 8,236,049 | B2 | 8/2012 | Rowe et al. |
| 8,252,042 | B2 | 8/2012 | McNamara et al. |
| 8,252,051 | B2 | 8/2012 | Chau |
| 8,252,052 | B2 | 8/2012 | Salahieh et al. |
| 8,257,390 | B2 | 9/2012 | Carley et al. |
| 8,267,988 | B2 | 9/2012 | Hamer et al. |
| 8,277,501 | B2 | 10/2012 | Chalekian et al. |
| 8,287,591 | B2 | 10/2012 | Keidar et al. |
| 8,298,280 | B2 | 10/2012 | Yadin et al. |
| 8,303,653 | B2 | 11/2012 | Bonhoeffer et al. |
| 8,308,798 | B2 | 11/2012 | Pintor et al. |
| 8,317,853 | B2 | 11/2012 | Agnew |
| 8,317,855 | B2 | 11/2012 | Gregorich et al. |
| 8,323,335 | B2 | 12/2012 | Rowe et al. |
| 8,328,868 | B2 | 12/2012 | Paul et al. |
| 8,337,541 | B2 | 12/2012 | Quadri et al. |
| 8,343,174 | B2 | 1/2013 | Goldfarb et al. |
| 8,343,213 | B2 | 1/2013 | Salahieh et al. |
| 8,348,999 | B2 | 1/2013 | Kheradvar et al. |
| 8,366,767 | B2 | 2/2013 | Zhang |
| 8,372,140 | B2 | 2/2013 | Hoffman et al. |
| 8,377,119 | B2 | 2/2013 | Drews et al. |
| 8,398,708 | B2 | 3/2013 | Meiri et al. |
| 8,403,981 | B2 | 3/2013 | Forster et al. |
| 8,403,983 | B2 | 3/2013 | Quadri et al. |
| 8,408,214 | B2 | 4/2013 | Spenser |
| 8,414,644 | B2 | 4/2013 | Quadri et al. |
| 8,425,593 | B2 | 4/2013 | Braido et al. |
| 8,430,934 | B2 | 4/2013 | Das |
| 8,444,689 | B2 | 5/2013 | Zhang |
| 8,449,599 | B2 | 5/2013 | Chau et al. |
| 8,449,625 | B2 | 5/2013 | Campbell et al. |
| 8,454,686 | B2 | 6/2013 | Alkhatib |
| 8,460,365 | B2 | 6/2013 | Haverkost et al. |
| 8,474,460 | B2 | 7/2013 | Barrett et al. |
| 8,512,400 | B2 | 8/2013 | Tran et al. |
| 8,539,662 | B2 | 9/2013 | Stacchino et al. |
| 8,545,544 | B2 | 10/2013 | Spenser et al. |
| 8,551,160 | B2 | 10/2013 | Figulla et al. |
| 8,551,161 | B2 | 10/2013 | Dolan |
| 8,562,672 | B2 | 10/2013 | Bonhoeffer et al. |
| 8,579,964 | B2 | 11/2013 | Lane et al. |
| 8,579,965 | B2 | 11/2013 | Bonhoeffer et al. |
| 8,585,755 | B2 | 11/2013 | Chau et al. |
| 8,585,756 | B2 | 11/2013 | Bonhoeffer et al. |
| 8,591,460 | B2 | 11/2013 | Wilson et al. |
| 8,591,570 | B2 | 11/2013 | Revuelta et al. |
| 8,623,075 | B2 | 1/2014 | Murray, III et al. |
| 8,623,080 | B2 | 1/2014 | Fogarty et al. |
| 8,628,569 | B2 | 1/2014 | Benichou et al. |
| 8,628,570 | B2 | 1/2014 | Seguin |
| 8,628,571 | B1 | 1/2014 | Hacohen et al. |
| 8,652,203 | B2 | 2/2014 | Quadri et al. |
| 8,652,204 | B2 | 2/2014 | Quill et al. |
| 8,657,872 | B2 | 2/2014 | Seguin |
| 8,663,322 | B2 | 3/2014 | Keranen |
| 8,673,020 | B2 | 3/2014 | Sobrino-Serrano et al. |

(56) References Cited

U.S. PATENT DOCUMENTS

| | | | |
|---|---|---|---|
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 * | 10/2014 | Gross ............... A61F 2/2439 623/1.26 |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,992,599 B2 | 3/2015 | Thubrikar et al. |
| 8,992,604 B2 | 3/2015 | Gross et al. |
| 8,998,982 B2 * | 4/2015 | Richter ............ A61F 2/2409 623/2.14 |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 * | 5/2015 | Quadri ............ A61F 2/2418 623/2.11 |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich, Jr. et al. |
| 9,072,603 B2 | 7/2015 | Tuval et al. |
| 9,084,676 B2 | 7/2015 | Chau et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,136,312 B2 | 9/2015 | Tuval et al. |
| 9,173,738 B2 | 11/2015 | Murray, III et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman, III et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 * | 7/2016 | Gross ............... A61F 2/2439 |
| 9,421,098 B2 | 8/2016 | Gifford, III et al. |
| 9,427,303 B2 | 8/2016 | Liddy et al. |
| 9,427,316 B2 | 8/2016 | Schweich, Jr. et al. |
| 9,474,638 B2 | 10/2016 | Robinson et al. |
| 9,480,559 B2 | 11/2016 | Vidlund et al. |
| 9,498,314 B2 | 11/2016 | Behan |
| 9,532,870 B2 | 1/2017 | Cooper et al. |
| 9,554,897 B2 | 1/2017 | Lane et al. |
| 9,566,152 B2 | 2/2017 | Schweich, Jr. et al. |
| 9,629,716 B2 | 4/2017 | Seguin |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,817 B2 | 9/2017 | Roeder |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrisan et al. |
| 2002/0177894 A1 | 11/2002 | Acosta et al. |
| 2003/0036791 A1 | 2/2003 | Philipp et al. |
| 2003/0060875 A1 | 3/2003 | Wittens |
| 2003/0069635 A1 | 4/2003 | Cartledge et al. |
| 2003/0074052 A1 | 4/2003 | Besselink |
| 2003/0083742 A1 | 5/2003 | Spence et al. |
| 2003/0158578 A1 | 5/2003 | Pantages et al. |
| 2003/0105519 A1 | 6/2003 | Fasol et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright, Jr. et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 * | 10/2005 | Bergheim ............ A61B 8/445 606/108 |
| 2005/0251251 A1 | 11/2005 | Cribier |
| 2005/0267573 A9 | 12/2005 | Macoviak et al. |
| 2006/0004439 A1 | 1/2006 | Spenser et al. |
| 2006/0015171 A1 | 1/2006 | Armstrong |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0047297 A1 | 3/2006 | Case |

(56) References Cited

U.S. PATENT DOCUMENTS

| | | |
|---|---|---|
| 2006/0089627 A1 | 4/2006 | Burnett et al. |
| 2006/0111773 A1 | 5/2006 | Rittgers et al. |
| 2006/0116750 A1 | 6/2006 | Hebert et al. |
| 2006/0135964 A1 | 6/2006 | Vesely |
| 2006/0155357 A1 | 7/2006 | Melsheimer |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1* | 11/2006 | Artof .............. A61F 2/2418 623/2.18 |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1* | 1/2009 | Goetz .............. A61F 2/2418 623/2.18 |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quadri |
| 2009/0319037 A1 | 12/2009 | Rowe et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0114299 A1 | 5/2010 | Ben Muvhar et al. |
| 2010/0131054 A1 | 5/2010 | Tuval et al. |
| 2010/0137979 A1 | 6/2010 | Tuvai et al. |
| 2010/0160958 A1 | 6/2010 | Clark |
| 2010/0161036 A1* | 6/2010 | Pintor .............. A61F 2/2418 623/1.26 |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0255737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0324595 A1 | 12/2010 | Linder et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fenster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |

(56) References Cited

U.S. PATENT DOCUMENTS

| | | |
|---|---|---|
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1* | 9/2011 | Hacohen ............ A61B 17/0401 623/2.18 |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1* | 11/2011 | Thill ............ A61F 2/2418 623/2.17 |
| 2011/0282440 A1 | 11/2011 | Cao et al. |
| 2011/0283514 A1 | 11/2011 | Fogarty et al. |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0313515 A1 | 12/2011 | Quadri et al. |
| 2011/0319989 A1* | 12/2011 | Lane ............ A61F 2/2418 623/2.11 |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0148891 A1 | 5/2014 | Johnson |
| 2014/0163690 A1 | 6/2014 | White |
| 2014/0172069 A1 | 6/2014 | Roeder et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1* | 7/2014 | Hacohen ............ A61F 2/2427 623/2.11 |
| 2014/0214159 A1 | 7/2014 | Vidlund et al. |
| 2014/0222136 A1 | 8/2014 | Geist et al. |
| 2014/0249622 A1 | 9/2014 | Carmi et al. |
| 2014/0257461 A1 | 9/2014 | Robinson et al. |
| 2014/0257467 A1* | 9/2014 | Lane ............ A61F 2/2412 623/2.11 |
| 2014/0257475 A1 | 9/2014 | Gross et al. |

(56) References Cited

U.S. PATENT DOCUMENTS

| | | |
|---|---|---|
| 2014/0257476 A1 | 9/2014 | Montorfano et al. |
| 2014/0277358 A1 | 9/2014 | Slazas |
| 2014/0277409 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142103 A1 | 5/2015 | Vidlund |
| 2015/0164640 A1 | 6/2015 | McLean et al. |
| 2015/0173896 A1* | 6/2015 | Richter .............. A61F 2/2409 623/2.11 |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1* | 10/2015 | Melnick .............. A61F 2/2418 623/2.11 |
| 2015/0282964 A1 | 10/2015 | Beard et al. |
| 2015/0320556 A1 | 11/2015 | Levi et al. |
| 2015/0327994 A1* | 11/2015 | Morriss .............. A61F 2/2418 623/2.17 |
| 2015/0328000 A1 | 11/2015 | Ratz et al. |
| 2015/0335429 A1 | 11/2015 | Morriss et al. |
| 2015/0359629 A1 | 12/2015 | Ganesan et al. |
| 2016/0030171 A1 | 2/2016 | Quijano et al. |
| 2016/0095700 A1 | 4/2016 | Righini |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0310268 A1 | 10/2016 | Oba et al. |
| 2016/0317301 A1 | 11/2016 | Quadri et al. |
| 2016/0324633 A1 | 11/2016 | Gross et al. |
| 2016/0324640 A1 | 11/2016 | Gifford, III et al. |
| 2016/0331526 A1 | 11/2016 | Schweich, Jr. et al. |
| 2017/0042678 A1 | 2/2017 | Ganesan et al. |
| 2017/0056171 A1 | 3/2017 | Cooper et al. |
| 2017/0128205 A1 | 5/2017 | Tamir et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0153689 A1 | 6/2018 | Maimon et al. |
| 2018/0177594 A1 | 6/2018 | Patel et al. |

FOREIGN PATENT DOCUMENTS

| | | |
|---|---|---|
| WO | 98/43557 A1 | 10/1998 |
| WO | 99/30647 A1 | 6/1999 |
| WO | 00/47139 A1 | 8/2000 |
| WO | 01/62189 A1 | 8/2001 |
| WO | 01/87190 A2 | 11/2001 |
| WO | 03/028558 A2 | 4/2003 |
| WO | 2006007401 A2 | 1/2006 |
| WO | 2006/054930 A1 | 5/2006 |
| WO | 2006/070372 A2 | 7/2006 |
| WO | 2006/089236 A1 | 8/2006 |
| WO | 2007/059252 A1 | 5/2007 |
| WO | 2008/013915 A3 | 1/2008 |
| WO | 2008/029296 A2 | 3/2008 |
| WO | 2008/070797 A2 | 6/2008 |
| WO | 2008/103722 A2 | 8/2008 |
| WO | 2009/033469 A1 | 3/2009 |
| WO | 2009/053497 A1 | 4/2009 |
| WO | 2009/091509 A1 | 7/2009 |
| WO | 2010/006627 A1 | 1/2010 |
| WO | 2010/073246 A2 | 7/2010 |
| WO | 2010/081033 A1 | 7/2010 |
| WO | 2011025972 A2 | 3/2011 |
| WO | 2011/069048 A2 | 9/2011 |
| WO | 2011/106137 A1 | 9/2011 |
| WO | 2011/111047 A2 | 9/2011 |
| WO | 2011/143263 A2 | 11/2011 |
| WO | 2011137531 A1 | 11/2011 |
| WO | 2011/154942 A2 | 12/2011 |
| WO | 2012/011108 A2 | 1/2012 |
| WO | 2012/024428 A2 | 2/2012 |
| WO | 2012/036740 A2 | 3/2012 |
| WO | 2012/127309 A1 | 9/2012 |
| WO | 2012/177942 A2 | 12/2012 |
| WO | 2013/021374 A2 | 2/2013 |
| WO | 2013/021375 A2 | 2/2013 |
| WO | 2013/021384 A1 | 2/2013 |
| WO | 2013/059747 A1 | 4/2013 |
| WO | 2013/078497 A1 | 6/2013 |
| WO | 2013/128436 A1 | 9/2013 |
| WO | 2014/022124 A1 | 2/2014 |
| WO | 2014/0145338 A1 | 9/2014 |
| WO | 2014/164364 A1 | 10/2014 |
| WO | 2015/173794 A1 | 11/2015 |
| WO | 2016/093877 A1 | 6/2016 |
| WO | 2017/223486 A1 | 12/2017 |
| WO | 2018/025260 A1 | 2/2018 |
| WO | 2018/106837 A1 | 6/2018 |
| WO | 2018/112429 A1 | 6/2018 |
| WO | 2018/118717 A1 | 6/2018 |
| WO | 2018/131042 A1 | 7/2018 |
| WO | 2018/131043 A1 | 7/2018 |

OTHER PUBLICATIONS

Invitation to pay additional fees dated Sep. 29, 2017; PCT/IL2017/050873.

Alexander S. Geha, et al; "Replacement of Degenerated Mitral and Aortic Bioprostheses Without Explantation", Ann Thorac Surg; Jun. 2001; 72:1509-1514.

Dominique Himbert; "Mitral Regurgitation and Stensos from Bioprosthesis and Annuloplasty Failure: Transcatheter approaches and outcomes", 24 pages, Oct. 26, 2013.

J. Jansen, et al; "Detachable shape-memory sewing ring for heart valves", Artificial Organs, 16:294-297, 1992 (abstract only).

Frank Langer: "RING plus STRING: Papillary muscle repositioning as an adjunctive repair technique for ischemic mitral regurgitation", J. Thorac Cardiovasc Surg; 133:247-9, Jan. 2007.

Frank Langer, et al; "RING+STRING Successful Repair Technique for Ischemic Mitral Regurgitation With Severe Leaflet Tethering", Circulation 120[suppl 1]: S85-S91, Sep. 2009.

Francesco Maisano; "Valtech Cardiovalve: Novel Design Feature and Clinical Update", TCR 2015 presentation re Cardiovalve.

John G. Webb, et al; "Transcatheter Valve-in-Valve Implantation for Failed Bioprosthetic Heart Valves", Circulation Apr. 2010; 121: 1848-1857.

Extended European Search Report dated Feb. 18, 2015; Appln. 12821522.5-1651/2739214 PCT/IL2012000293.

Invitation to Pay Additional Fees; dated Jun. 12, 2014, PCT/IL2014/050087.

International Preliminary Report on Patentability dated Dec. 2, 2013; PCT/IL2011/000582.

(56) References Cited

OTHER PUBLICATIONS

International Preliminary Report on Patentability dated Sep. 11, 2012; PCT/IL2011/000231.
International Preliminary Report on Patentability dated Feb. 11, 2014, PCT/IL2012/000292.
International Preliminary Report on Patentability dated Feb. 11, 2014; PCT/IL2012/000293.
International Search Report and Written Opinion dated Feb. 6, 2013; PCT/IL12/00292.
International Search Report and Written Opinion dated Feb. 6, 2013; PCT/IL2012/000293.
International Search Report and Written Opinion dated Mar. 17, 2014; PCT/IL13/50937.
International Search Report and Written Opinion dated May 30, 2016; PCT/IL2016/050125.
International Search Report and Written Opinion dated Sep. 4, 2014; PCT/IL2014/050087.
International Search Report and Written Opinion dated Oct. 13, 2011; PCT/IL11/00231.
International Search Report and Written Opinion dated Oct. 27, 2015; PCT/IL2015/050792.
International Search Report and Written Opinion dated Dec. 5, 2011; PCT/IL11/00582.
U.S. Appl. No. 61/283,819, filed Dec. 8, 2009.
U.S. Appl. No. 61/492,449, filed Jun. 2, 2011.
U.S. Appl. No. 61/515,372, filed Aug. 5, 2011.
U.S. Appl. No. 61/525,281, filed Aug. 19, 2011.
U.S. Appl. No. 61/537,276, filed Sep. 21, 2011.
U.S. Appl. No. 61/555,160, filed Nov. 3, 2011.
U.S. Appl. No. 61/588,892, filed Jan. 20, 2012.
Righini presentation EuroPCR May 2015 (Saturn)—(downloaded from: https://www.pcronline.com/Cases-resourcesimages/Resources/Course-viedeos-slides/2015/Cardiovascularinnovation-pipeline-Mitral-and-triscupid-valve-interventions), 18 pages.
Saturn Project—a novel solution for transcatheter heart valve replacement specifically designed to address clinical therapeutic needs on mitral valve: Dec. 2016, 8 pages.
EPO Office Action dated Feb. 10, 2017; Appln. No. 12 821 522.5-1651.
UK Office Action dated Feb. 8, 2017; Appln. No. GB1613219.3.
USPTO NFOA dated Jan. 18, 2017 in connection with U.S. Appl. No. 14/626,267.
USPTO NFOA dated Feb. 7, 2017 in connection with U.S. Appl. No. 14/689,608.
USPTO NFOA dated May 29, 2012 in connection with U.S. Appl. No. 12/840,463.
USPTO FOA dated Feb. 15, 2013 in connection with U.S. Appl. No. 12/840,463.
USPTO NFOA dated Nov. 8, 2013 in connection with U.S. Appl. No. 12/840,463.
USPTO NFOA dated Jun. 4, 2014 in connection with U.S. Appl. No. 12/840,463.
USPTO FOA dated Mar. 25, 2015 in connection with U.S. Appl. No. 12/840,463.
USPTO NOA dated May 5, 2015 in connection with U.S. Appl. No. 12/840,463.
USPTO RR dated Aug. 14, 2012 in connection with U.S. Appl. No. 12/961,721.
USPTO NFOA dated Nov. 28, 2012 in connection with U.S. Appl. No. 12/961,721.
USPTO FOA dated Jul. 23, 2013 in connection with U.S. Appl. No. 12/961,721.
USPTO NFOA dated Jun. 17, 2014 in connection with U.S. Appl. No. 12/961,721.
USPTO RR dated Jul. 2, 2012 in connection with U.S. Appl. No. 13/033,852.
USPTO NFOA dated Nov. 23, 2012 in connection with U.S. Appl. No. 13/033,852.
USPTO NFOA dated Aug. 2, 2013 in connection with U.S. Appl. No. 13/033,852.
USPTO FOA dated Feb. 10, 2014 in connection with U.S. Appl. No. 13/033,852.
USPTO NFOA dated Jul. 3, 2014 in connection with U.S. Appl. No. 13/033,852.
USPTO NOA dated Feb. 11, 2015 in connection with U.S. Appl. No. 13/033,852.
USPTO RR dated Aug. 13, 2012 in connection with U.S. Appl. No. 13/044,694.
USPTO NFOA dated Dec. 31, 2012 in connection with U.S. Appl. No. 13/044,694.
USPTO FOA dated Jul. 18, 2013 in connection with U.S. Appl. No. 13/044,694.
USPTO NFOA dated Sep. 19, 2014 in connection with U.S. Appl. No. 13/044,694.
USPTO NFOA dated Feb. 6, 2013 in connection with U.S. Appl. No. 13/412,814.
USPTO NFOA dated Sep. 12, 2013 in connection with U.S. Appl. No. 13/412,814.
USPTO FOA dated May 23, 2014 in connection with U.S. Appl. No. 13/412,814.
USPTO NOA dated Aug. 15, 2014 in connection with U.S. Appl. No. 13/412,814.
USPTO RR dated Feb. 3, 2014 in connection with U.S. Appl. No. 13/811,308.
USPTO NFOA dated Jul. 2, 2014 in connection with U.S. Appl. No. 13/811,308.
USPTO NOA dated Mar. 10, 2015 in connection with U.S. Appl. No. 13/811,308.
USPTO RR dated Jan. 20, 2016 in connection with U.S. Appl. No. 14/161,921.
USPTO NFOA dated Dec. 10, 2015 in connection with U.S. Appl. No. 14/237,258.
USPTO RR dated Aug. 28, 2015 in connection with U.S. Appl. No. 14/237,264.
USPTO NFOA dated Jan. 21, 2016 in connection with U.S. Appl. No. 14/237,264.
USPTO NOA dated Apr. 8, 2016 in connection with U.S. Appl. No. 14/237,258.
USPTO Supplemental NOA dated May 10, 2016 in connection with U.S. Appl. No. 14/237,258.
USPTO Supplemental NOA dated May 20, 2016 in connection with U.S. Appl. 14/237,258.
USPTO NFOA dated Jun. 30, 2015 in connection with U.S. Appl. 14/522,987.
USPTO FOA dated Feb. 25, 2016 in connection with U.S. Appl. No. 14/522,987.
USPTO NFOA dated Nov. 27, 2015 in connection with U.S. Appl. No. 14/626,267.
USPTO FOA dated Apr. 13, 2016 in connection with U.S. Appl. No. 14/626,267.
USPTO RR dated Sep. 26, 2016 in connection with U.S. Appl. No. 14/763,004.
USPTO NFOA dated Oct. 23, 2017 in connection with U.S. Appl. No. 14/763,004.
USPTO FDA dated Jan. 17, 2018 in connectien with U.S. Appl. No. 14/763,004.
USPTO NFOA dated Dec. 7, 2017 in connection with U.S. Appl. No. 15/213,791.
Interview Summary dated Feb. 8, 2018 in conncection with U.S. Appl. No. 15/213,791.
USPTO NFOA dated Jan. 5, 2018 in connection with U.S. Appl. No. 15/541,783.
USPTO NFOA dated Feb. 2, 2018 in connection with U.S. Appl. No. 15/329,920.
Invitation to pay additional fees dated Jan. 2, 2018; PCT/IL2017/050849.
An Office Action dated Jun. 6, 2018, which issued during the prosecution of UK Patent Application No. 1720803.4.
An Office Action dated Jun. 18, 2018, which issued during the prosecution of UK Patent Application No. 1800399.6.
International Search Report and Written Opinion dated Jun. 20, 2018 PCT/IL2018/050024.

(56) References Cited

OTHER PUBLICATIONS

USPTO AA dated Apr. 2, 2018 in connection with U.S. Appl. No. 14/763,004.
USPTO NFOA dated Jun. 28, 2018 in connection with U.S. Appl. No. 29/635,658.
USPTO NFOA dated Jun. 28, 2018 in connection with U.S. Appl. No. 29/635,661.
USPTO NFOA dated Jul. 26, 2018 in connection with U.S. Appl. No. 15/872,501.
USPTO NFOA dated Aug. 9, 2018 in connection with U.S. Appl. No. 15/899,858.
USPTO NOA dated Apr. 20, 2018 in connection with U.S. Appl. No. 15/878,206.
USPTO RR dated May 4, 2018 in connection with U.S. Appl. No. 15/872,501.
USPTO NFOA dated Apr. 20, 2018 in connection with U.S. Appl. No. 15/886,517.
USPTO NFOA dated Aug. 9, 2018 in connection with U.S. Appl. No. 15/902,403.

* cited by examiner

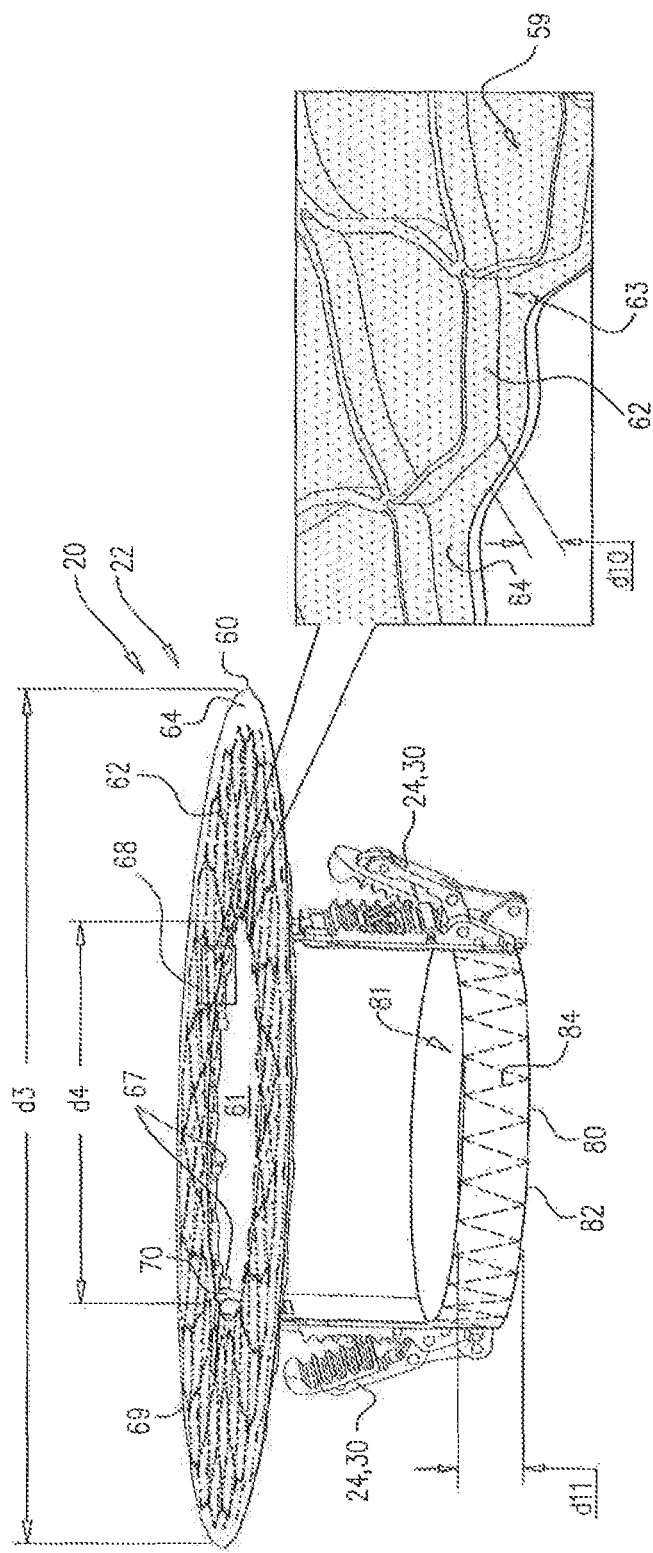

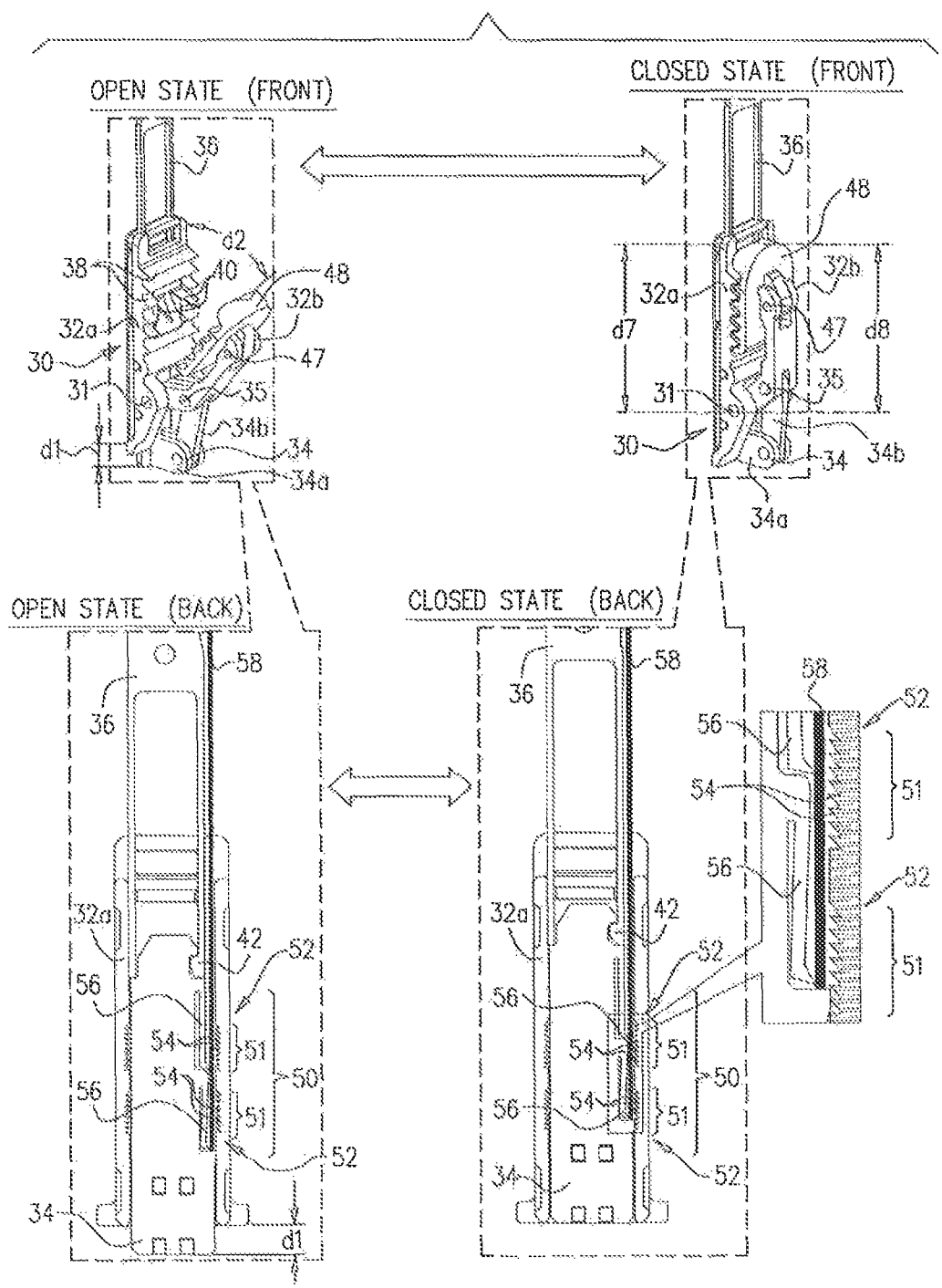

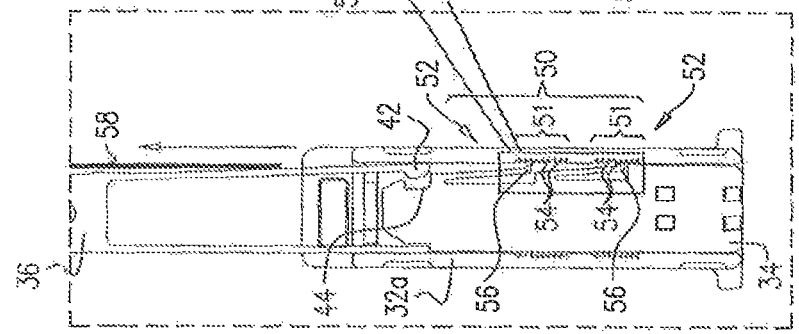
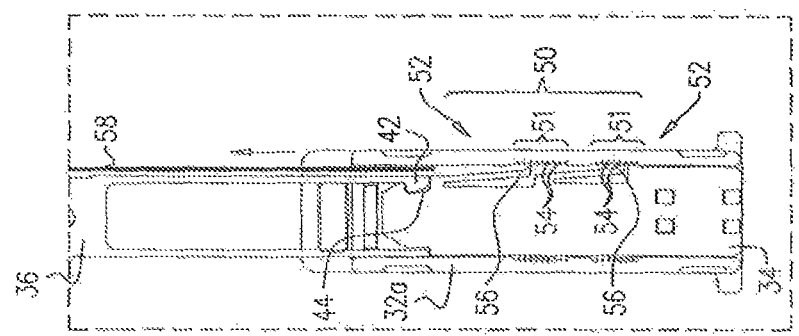

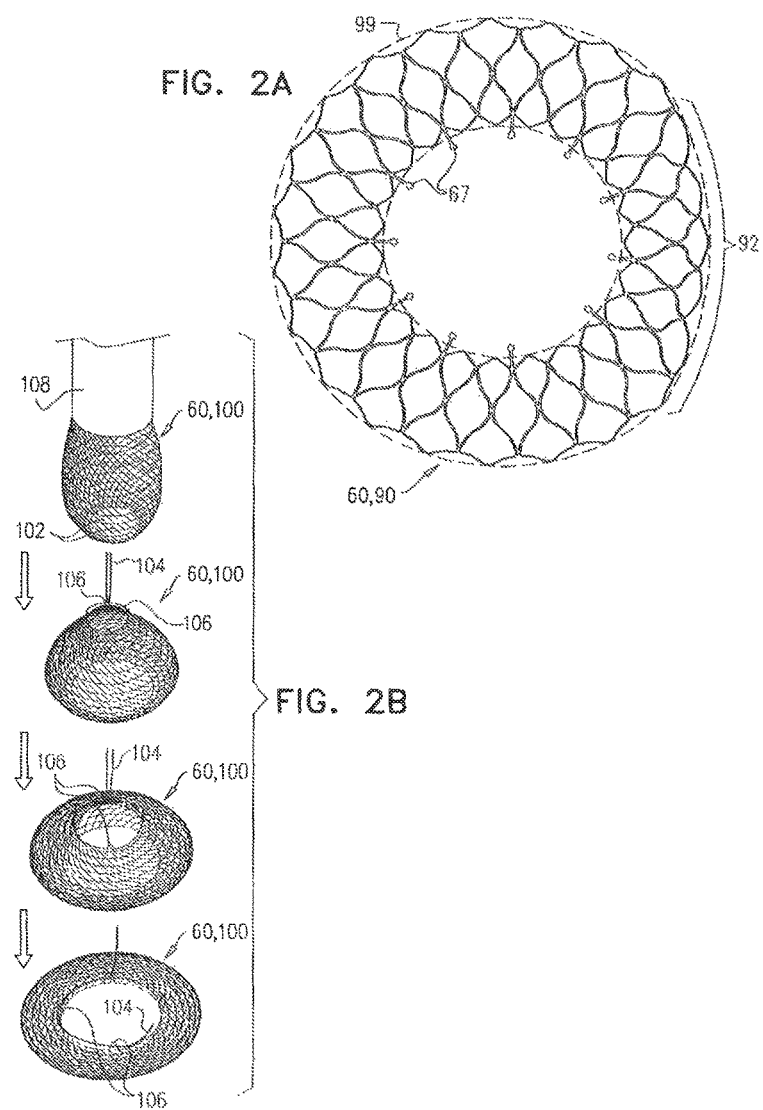

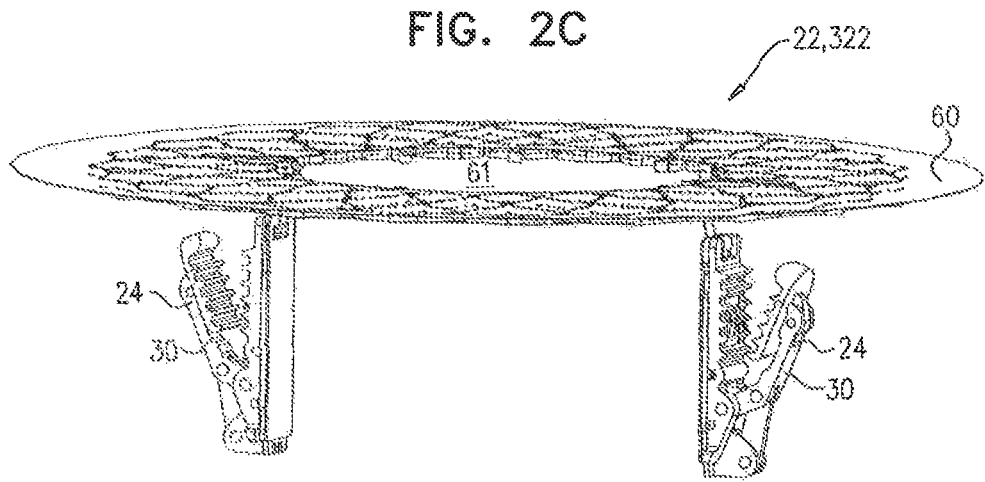
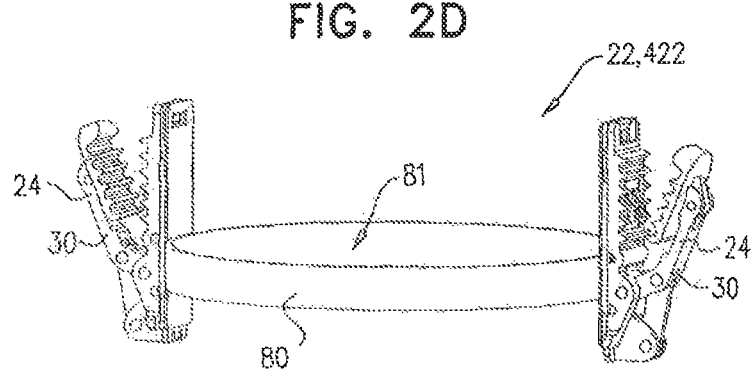

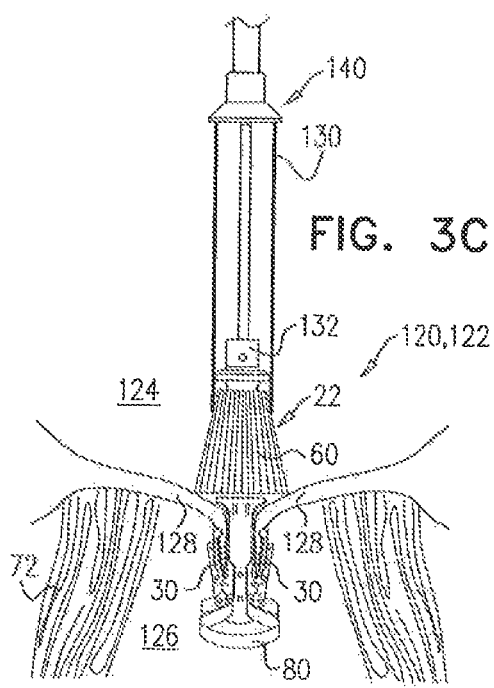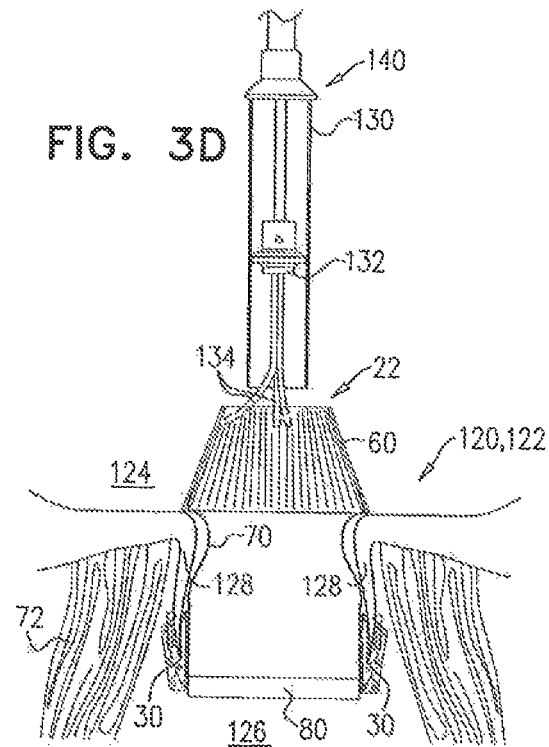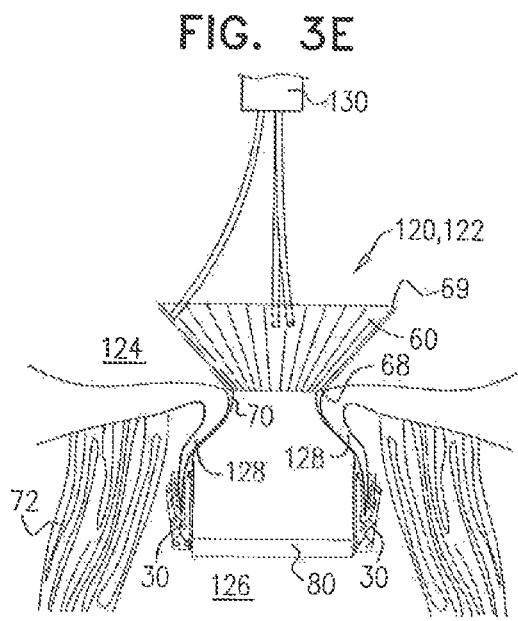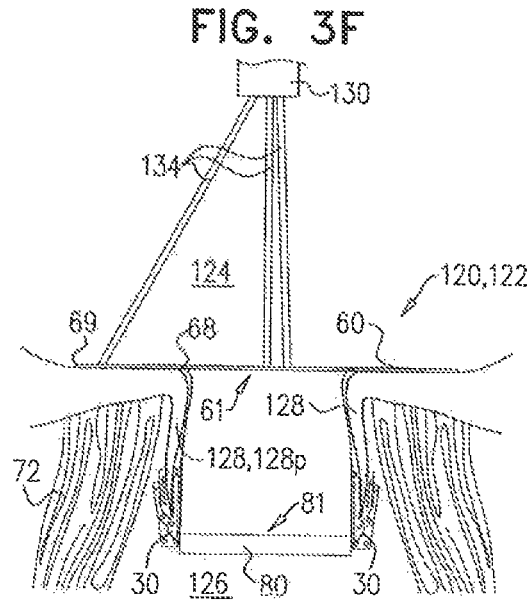

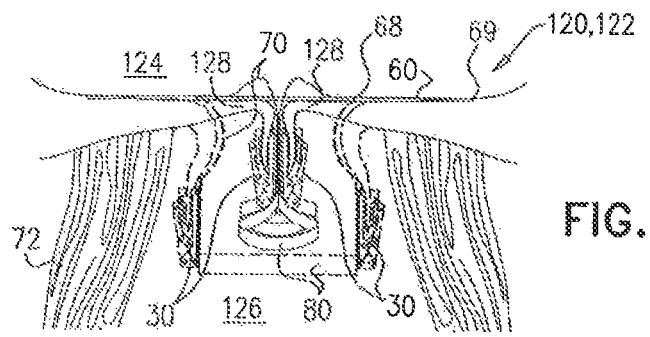
FIG. 3G
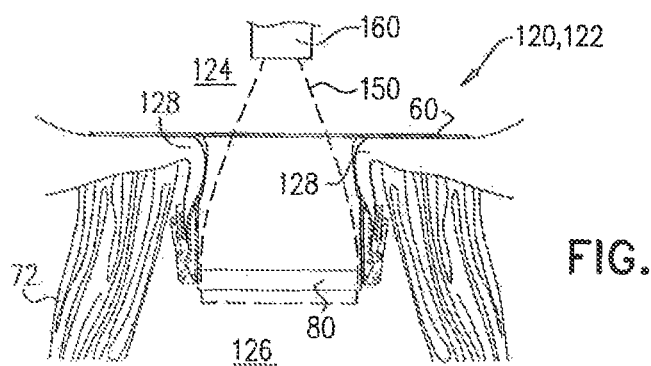
FIG. 3H
FIG. 3I
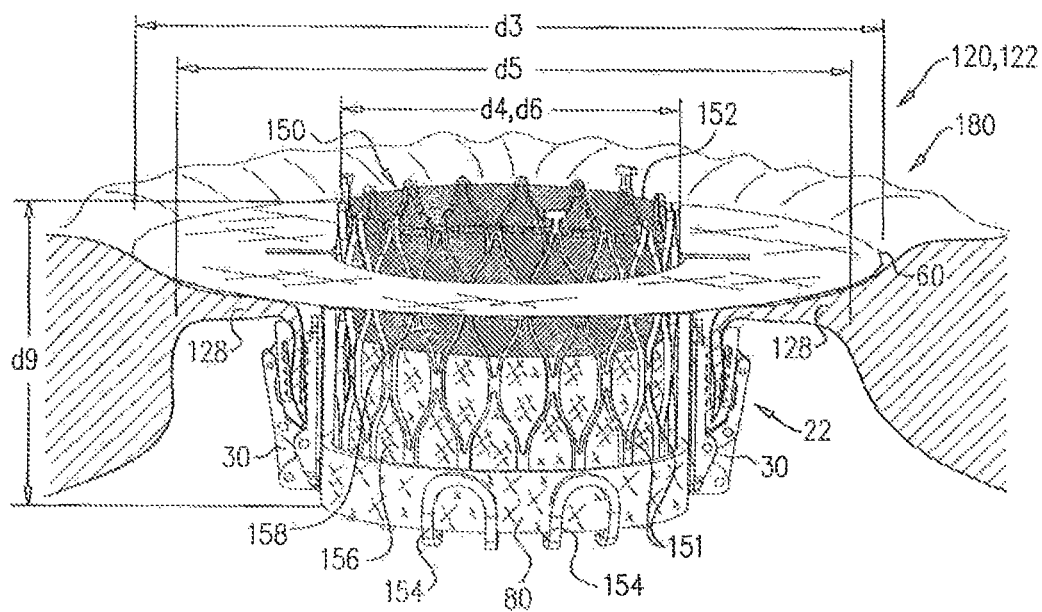

IMPLANT FOR HEART VALVE

CROSS-REFERENCES TO RELATED APPLICATIONS

This application is a Continuation of U.S. Ser. No. 14/237,158 to Gross et al., which published as US 2014/0257475, and which is the US National phase of PCT Patent Application IL2012/000293 to Gross et al., which published as WO 2013/021375, and which:
(1) claims priority from:
U.S. 61/515,372 to Gross, filed Aug, 5, 2011;
U.S. 61/525,281 to Gross, filed Aug. 19, 2011;
U.S. 61/537,276 to Gross, filed Sep. 21, 2011;
U.S. 61/555,160 to Gross, filed Nov, 3, 2011;
U.S. 61/588,892 to Gross, filed Jan. 20, 2012; and
U.S. Ser. No. 13/412,814 to Gross et al., filed Mar. 6, 2012,which published as US 2013/0035759 (now U.S. Pat. No. 8,852,272),all of which are incorporated herein by reference; and
(2) is a continuation-in-part of U.S, Ser. No. 13/412,814 to Gross et al., filed Mar. 6, 2012, which published as US 2013/0035759(now U.S. Pat. No. 8,852,272).

This application is related to PCT application IL2012/000292 to Gross et al, entitled, "Techniques for percutaneous mitral valve replacement and sealing," filed on even date herewith, which published as WO 2013/021374.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications of the invention, a prosthetic valve support is provided for facilitating minimally invasive (e.g., transcatheter and/or transluminal) implantation of a prosthetic valve at a native valve of a subject. The native valve typically has native check valve functionality, i.e., it functions as a check valve. It is understood that a diseased valve has sub-optimal native check valve functionality, however the term "check valve functionality," as used in the context of the specification and in the claims, when used with respect to a native valve, refers to the native level of check valve functionality of the native valve. The prosthetic valve support is typically couplable to the native valve (e.g., to leaflets thereof) of the subject without eliminating the check valve functionality of the native valve. The prosthetic valve is subsequently implanted at the native valve by coupling the prosthetic valve to the prosthetic valve support, typically by expanding the prosthetic valve within one or more openings defined by the prosthetic valve support. The implantation of the prosthetic valve at the native valve replaces, at least in part, the check valve functionality of the native valve with substitute check valve functionality of the prosthetic valve. The prosthetic valve support comprises tissue-engaging elements, such as clips. Typically, but not necessarily, the prosthetic valve support further comprises (1) an upstream support portion, configured to be placed against an upstream surface of the native valve, and shaped to define one of the openings, and (2) a stabilizing element, shaped to define another of the openings.

For some applications, the prosthetic valve support is configured to be coupled to the native valve (e.g., to leaflets thereof) without eliminating the check valve functionality of the native valve, by allowing (1) the native leaflets to define a single orifice, and (2) the native valve to function as a single check valve (e.g., to function in a manner that is generally similar to the natural (e.g., physiological) function of the native valve). For some applications, the prosthetic valve support is configured to be coupled to the native valve (e.g., to leaflets thereof) without eliminating the check valve functionality by coupling together respective portions of two leaflets, such that (1) the native leaflets define two orifices, and (2) the native valve functions as two (e.g., parallel) check valves.

For some applications, it is hypothesized that the use of a two-component implant (i.e., comprising the prosthetic valve support and a separate prosthetic valve), advantageously facilitates delivery of the prosthetic valve via a catheter narrower than 28 Fr (e.g., by allowing the use of a 'minimalistic' prosthetic valve, such as a prosthetic valve with few or no appendages).

For some applications, it is hypothesized that the use of a prosthetic valve support that does not eliminate check valve functionality of the native valve, facilitates the separate delivery of the prosthetic valve support and the prosthetic valve (i.e., a two-stage delivery), and thereby further facilitates the use of a narrow catheter.

For some applications, it is further hypothesized that the use of the prosthetic valve support enhances the check valve functionality of the native valve, and thereby provides both (1) "repair" of the native valve, and (2) an implantation site that is pre-prepared for subsequent implantation of a prosthetic valve at a later date, should such implantation be subsequently considered necessary.

There is therefore provided, in accordance with an application of the present invention, apparatus for use with a prosthetic valve for implantation at a native valve of a subject, the native valve including at least one native leaflet, the apparatus including:
a prosthetic valve support, including:
an upstream support portion, being configured to be placed against an upstream side of the native valve, and having an inner perimeter that defines an opening that is configured to receive the prosthetic valve, and
at least one clip:
including at least two clip arms and a clip-controller interface, the clip-controller interface being coupled to at least one of the clip arms, and
being configured to be coupled to a native leaflet of the native valve; and
at least one clip controller, reversibly couplable to the clip-controller interface, and configured to facilitate opening and closing of the clip.

In an application, the at least two clip arms include a first clip arm, configured to be disposed against an upstream surface of the leaflet, and a second clip arm, configured to be disposed against a downstream surface of the leaflet.

In an application, the clip controller is configured to facilitate opening and closing of the clip irrespective of a state of expansion of the prosthetic valve support.

In an application, the at least one clip includes at least a first clip and a second clip, and the second clip is openable and closeable independently of the first clip.

In an application, the at least one clip includes at least a first clip and a second clip, and the first clip is fixedly coupled to the second clip, and is configured to be decoupled from the second clip.

In an application, the at least one clip is configured to be coupled to a single native leaflet of the native valve.

In an application, the at least one clip is configured to be lockable such that the first clip arm is locked with respect to the second clip arm.

In an application:

the native valve includes at least a first native leaflet and a second native leaflet, the at least one clip includes at least a first clip and a second clip, the first clip being configured to be coupled to the first leaflet, and the second clip being configured to be coupled to the second leaflet, and the prosthetic valve support is configured such that, when (1) the upstream support portion is disposed against the upstream side of the native valve, (2) the first clip is coupled to the first leaflet, and (3) the second clip is coupled to the second leaflet, the first clip moves toward the second clip during ventricular systole of the subject, and moves away from the second clip during ventricular diastole of the subject.

In an application, the clip is flexibly coupled to the upstream support portion.

In an application, the clip is coupled to the upstream support portion via a flexible connector, the flexible connector having a length from the upstream support portion to the clip, and the length of the flexible connector is variable.

In an application, the upstream support portion is generally flat.

In an application, the inner perimeter defines the opening, such that the opening has a depth and a width, and the width of the opening is more than four times greater than the depth of the opening.

In an application, the upstream support portion has a free inner edge, and the free inner edge defines the inner perimeter.

In an application, the inner perimeter defines an opening that has a diameter, and the upstream support portion has a diameter that is at least 10 percent greater than the diameter of the opening.

In an application, no part of the prosthetic valve support that circumscribes a space that has a perimeter greater than 60 mm has a height of more than 20 mm.

There is further provided, in accordance with an application of the present invention, apparatus for facilitating implantation of a prosthetic valve at a native heart valve of a subject, the native heart valve including a native annulus and a plurality of native leaflets that provide check valve functionality, the apparatus including a prosthetic valve support:

being configured to be transluminally-delivered to the native valve and to be deployed at the native valve, and including one or more tissue-engaging elements, configured to couple the prosthetic valve support to the native leaflets without eliminating the check valve functionality.

In an application, the tissue-engaging elements are configured to couple the prosthetic valve support to the native leaflets without eliminating the check valve functionality, by coupling the prosthetic valve support to the native leaflets such that:

the native leaflets define a single orifice therebetween, and the native valve functions as a single check valve.

In an application, the tissue-engaging elements include at least a first tissue-engaging element and a second tissue-engaging element, and the first tissue-engaging element is transluminally controllable independently of the second tissue-engaging element.

In an application, the tissue-engaging elements are configured to couple the prosthetic valve support to the native leaflets without eliminating the check valve functionality, by coupling the prosthetic valve support to the native leaflets such that:

the native leaflets define two orifices therebetween, and the native valve functions as two check valves.

In an application:

the native leaflets include a first leaflet and a second leaflet, the tissue-engaging elements include at least a first tissue-engaging element and a second tissue-engaging element, the first tissue-engaging element is configured to be coupled to a portion of the first leaflet, and the second tissue-engaging element is configured to be coupled to a portion of the second leaflet and to the first tissue-engaging element.

In an application, the apparatus is configured such that the first tissue-engaging element is transluminally, intracorporeally decouplable from the second tissue-engaging element.

In an application, the prosthetic valve support includes an annular upstream support portion:

shaped to define an opening therethrough, coupled to the tissue-engaging elements, configured to be placed against an upstream surface of the native annulus, and configured to be transluminally, intracorporeally, coupled to the prosthetic valve.

In an application, the apparatus further includes the prosthetic valve, and the prosthetic valve includes a flexible netting at at least an upstream portion of the prosthetic valve, and the netting is configured to facilitate coupling of the prosthetic valve to the upstream support portion.

In an application, the prosthetic valve support includes one or more flexible connectors, and each tissue-engaging element is flexibly coupled to the upstream support portion by a respective flexible connector.

In an application, each flexible connector has a length, and is configured such that the length is variable while the tissue-engaging elements are coupled to the native leaflets.

In an application, the upstream support portion has a compressed configuration and an expanded configuration, and is configured (1) to be delivered to the native valve in the compressed configuration, and (2) to be expanded into the expanded configuration at the native valve.

In an application, the apparatus further includes one or more coupling leads, and the apparatus is configured such that the expansion of the upstream support portion is controllable using the coupling leads.

In an application, each coupling lead passes around at least a portion of the upstream support portion, and the apparatus is configured such that the upstream support portion is recompressible from the expanded configuration toward the compressed configuration, by pulling on the coupling leads.

In an application, the prosthetic valve support includes a downstream stabilizing element:
- shaped to define an opening therethrough,
- coupled to the tissue-engaging elements,
- configured to be placed entirely downstream of the native annulus, and
- configured to be coupled to the prosthetic valve.

In an application, the apparatus further includes the prosthetic valve, and the prosthetic valve includes a valve body and one or more valve-anchoring elements, the valve-anchoring elements being configured to sandwich the downstream stabilizing element between the valve-anchoring elements and the valve body.

In an application, the prosthetic valve support is configured to be coupled to the native leaflets such that no portion of the prosthetic valve support is disposed upstream of the native annulus.

In an application, the tissue-engaging elements include clips, each clip including a plurality of clip arms, including at least a first clip arm and a second clip arm, and configured to couple at least a portion of one of the native leaflets between the first and second clip arms.

In an application, the apparatus further includes a clip controller, configured to be advanced transluminally to the native valve, and each clip includes a clip-controller interface, configured to be reversibly coupled to the clip controller, and to facilitate extracorporeal control of the clips independently of deployment of the prosthetic valve support.

In an application, each clip is configured such that movement of at least a portion of the clip-controller interface by a first distance, changes a distance between a portion of the first clip arm and a portion of the second clip arm by a second distance that is more than 1.5 times greater than the first distance.

In an application, the tissue-engaging elements are configured to suturelessly couple the prosthetic valve support to the native leaflets.

In an application, the prosthetic valve support is configured to be transluminally, intracorporeally, couplable to the prosthetic valve.

There is further provided, in accordance with an application of the present invention, a method for use at a native valve of a subject, the native valve including at least one native leaflet that provides native check valve functionality, the method including:
- transluminally delivering a prosthetic valve support to the native valve;
- coupling a prosthetic valve support to the leaflet of the native valve without eliminating the native check valve functionality; and
- subsequently, replacing, at least in part, the native check valve functionality with a substitute check valve functionality, by coupling a prosthetic valve to the prosthetic valve support.

In an application:
- the prosthetic valve support includes at least one clip,
- the clip includes two or more clip arms and a clip-controller interface, and
- coupling the prosthetic valve support to the leaflet includes changing an angular disposition between the clip arms by moving the clip-controller interface.

There is further provided, in accordance with an application of the present invention, apparatus for use with a native heart valve of a subject, the apparatus including:
- a first expandable prosthetic valve component, including a crimpable frame, and configured to be transcatheterally advanceable toward the native valve while the first prosthetic valve component is in a crimped state thereof;
- a second expandable prosthetic valve component, including a crimpable frame, and configured to be transcatheterally advanceable toward the native valve, placeable in the native valve while the second prosthetic valve component is in a crimped state thereof, and couplable to the first prosthetic valve component, expansion of the second prosthetic valve component facilitating coupling of the second prosthetic valve component to the first prosthetic valve component; and
- one or more tissue-engagement elements, coupled to at least one of the prosthetic valve components, the tissue-engagement elements configured, when the prosthetic valve component is in an expanded state thereof, to extend from the prosthetic valve component, and to inhibit a proximal movement of the prosthetic valve component.

There is further provided, in accordance with an application of the present invention, apparatus for use with a prosthetic valve for implantation at a native valve of a subject, the native valve (1) defining an orifice, (2) including at least one native leaflet, having a native beating, and (3) baying a native blood flow regulation functionality, the apparatus including:
- a prosthetic valve support, including:
  - an upstream support portion, configured to be placed against an upstream side of the native valve, to have an inner perimeter that defines an opening that is configured to receive the prosthetic valve, and
  - at least one clip, configured to be coupled to a native leaflet of the native valve, the clip including a plurality of clip arms, at least one clip arm coupled to a clip-controller interface; and
- a clip controller, couplable to the clip-controller interface, and configured to control a relative angular disposition between the clip arms.

For some applications, techniques described herein are practiced in combination with techniques described in one or more of the references cited in the Background section and Cross-references section of the present patent application.

BRIEF DESCRIPTION OF THE DRAWINGS

FIGS. 1A-D are schematic illustrations of apparatus, comprising a prosthetic valve support, for facilitating implantation of a prosthetic heart valve at a native heart valve of a subject, in accordance with some applications of the invention;

FIGS. 2A-D are schematic illustrations of the prosthetic valve support, and components thereof, in accordance with respective applications of the invention;

FIGS. 3A-I are schematic illustrations of steps in the delivery and implantation of the prosthetic valve support at the native heart valve of the subject, and the use thereof to facilitate implantation of the prosthetic valve, in accordance with some applications of the invention;

DETAILED DESCRIPTION OF EMBODIMENTS

Figure 3A:
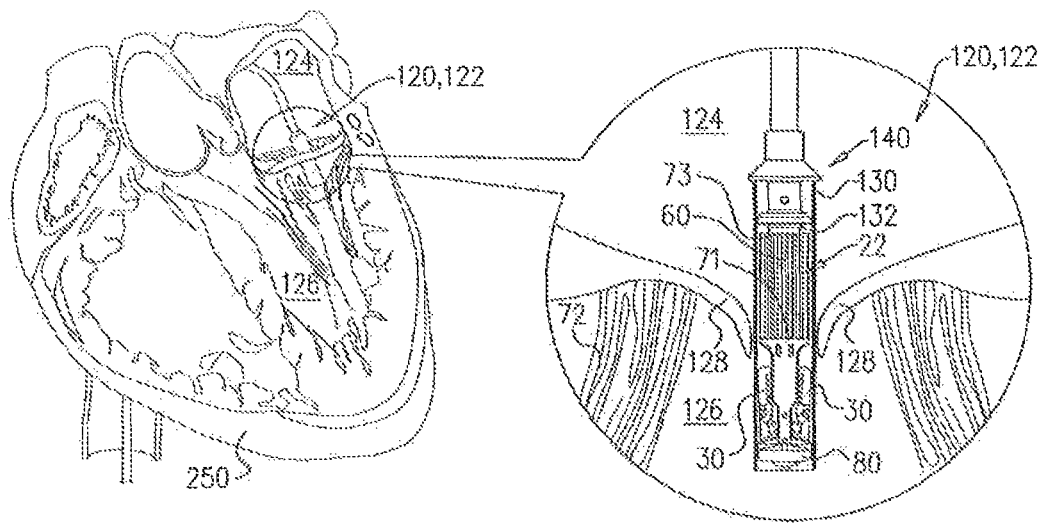

Reference is made to FIGS. 1A-D, which are schematic illustrations of apparatus 20, comprising a prosthetic valve support 22 for facilitating implantation of a prosthetic heart valve at a native heart valve of a subject, in accordance with some applications of the invention. Prosthetic valve support 22 comprises one or more tissue-engaging elements 24 (e.g., support-anchoring elements), and is typically configured to be coupled to the native heart valve (e.g., to leaflets thereof) without eliminating check valve functionality of the native heart valve (described in more detail hereinbelow). Typically, prosthetic valve 22 is configured to be transluminally, intracorporeally coupled to the native heart valve.

Typically, each tissue-engaging element 24 comprises a clip 30, which typically comprises a plurality of clip arms 32 (e.g., two clips arms, e.g., a first clip arm 32a and a second clip arm 32b), the clip being configured to be coupled to a leaflet of the native valve. Clip arms 32a and 32b are movable with respect to each other, thereby opening and closing clip 30 (e.g., moving clip 30 between an open state and a closed state thereof), e.g., as shown in FIG. 1B. Clip arms 32a and 32b are typically articulatably coupled to each other at an articulation point 31 (e.g., a coupling point), such that opening and closing clip 30 comprises changing a relative angular disposition between the clip arms. Typically, each clip arm 32 has a length from a first end thereof, at which the clip arms are coupled to each other (e.g., at articulation point 31), to a second end thereof, of greater than 1.5 mm and/or less than 20 mm (e.g., between 3 and 10 mm). For some applications, a length d7 of clip arm 32a is generally the same as a length d8 of clip arm 32b (e.g., as shown in FIG. 1B). For some applications, length d8 of clip arm 32b is shorter than length d7 of clip arm 32a (e.g., at least 30% shorter, such as at least 50% shorter), e.g., so as to reduce force applied to the leaflet of the native valve by clip arm 32b (such as by the second end of the clip arm).

For some applications of the invention, at least one of the clip arms (e.g., clip arm 32b) comprises a tissue-engaging portion 48 that is articulatably coupled to another portion of the clip arm at an articulation point 47, such that, at a given relative angular disposition of clip arms 32a and 32b (e.g., a degree of openness of clip 30), a relative angular disposition of portion 48 with respect to clip arm 32a, may change (e.g., may be changed). For example, for at least some states of clip 30, the relative angular disposition of clip arm 32a and portion 48 may be generally independent of the relative angular disposition of clip arm 32a and the other portion of clip arm 32b. For example, portion 48 may remain parallel with clip arm 32a, irrespective of the angular disposition of clip arms 32a and 32b. It is hypothesized that this configuration facilitates coupling of clip 30 to the leaflet of the native valve, by allowing the clip to maintain contact with both sides of the leaflet, irrespective of dimensions (e.g., thicknesses) of the leaflet to which clip 30 is coupled.

Prosthetic valve support 22 is typically configured to be implanted using minimally-invasive procedures (e.g., percutaneously). Further typically, the prosthetic valve support is configured to be delivered transluminally (e.g., transfemorally). Alternatively, the prosthetic valve support may be configured to be delivered transthoracically (e.g., transapically). Typically, the prosthetic valve support is configured in this way by being compressible (e.g., crimpable) into a delivery configuration, and by being configured to expand (e.g., automatically) upon deployment at the native valve. Typically, tissue-engaging elements 24 (e.g., clips 30) are coupled to the leaflets of the native valve before prosthetic valve support 22 is fully deployed, such as while at least part of the prosthetic valve support remains within a delivery tube (e.g., as shown in FIGS. 3B-C).

Clips 30 are typically configured to be controllable (i.e., openable and closable) independently of each other, and/or independently of deployment of prosthetic valve support 22 (e.g., irrespective of a state of deployment of the prosthetic valve support, such as irrespective of a state of expansion of an upstream support portion 60 of the prosthetic valve support, described hereinbelow).

Clip 30 typically further comprises a clip-controller interface 34, which is configured to facilitate control (e.g., opening and closing) of the clip from outside the subject (i.e., to facilitate extracorporeal control of the clip), e.g., by a physician. Clip-controller interface 34 is reversibly couplable to a clip controller 36, which is itself extracorporeally controllable, e.g., by extending from outside the subject to the clip-controller interface. Clip 30 is thereby typically transluminally controllable. Typically, clip controller 36 facilitates control of the clip by applying a force to clip-controller interface 34, e.g., by transferring an extracorporeally-applied force to the clip-controller interface. Typically, clip controller 36 is integral with delivery apparatus that is used to deliver support 22 to the native valve (e.g., delivery apparatus 140, described hereinbelow with reference to FIGS. 3A-D).

Clip-controller interface 34 is typically articulatably coupled to at least clip arm 32b (e.g., at an articulation point 35), and/or comprises one or more articulatably coupled portions (e.g., a first interface portion 34a and a second interface portion 34b). Clips 30 are typically configured such that movement of clip-controller interface 34 by a first distance d1, moves clip arm 32b by a second distance d2 that is typically more than 1.5 times (e.g., more than 2 times, such as more than 4 times) greater than distance d1. That is, a relatively large range of movement of clip arm 32b is provided by a relatively small range of movement of dip-controller interface 34, e.g., clip-controller interface 34, clip arm 32b, and/or the coupling therebetween, acts as a lever. Clip 30 is typically configured such that clip arm 32b can articulate over more than 60 degrees, e.g., more than 100 degrees, such as up to 180 degrees, around articulation point 31, with respect to clip arm 32a.

It is hypothesized that, for some applications, angles of articulation greater than 80 degrees (e.g., greater than 120 degrees, such as up to 180 degrees) facilitate (1) repeated coupling to, and decoupling from, the native leaflets (e.g., multiple attempts to couple to the native leaflets), and (2)

retrieval of the clips and/or the entire prosthetic valve support (e.g., into a delivery tube).

Clip-controller interface 34 (e.g., portion 34a thereof) is typically slidably coupled to at least clip arm 32a. That is, moving of clip-controller interface 34 typically includes sliding of the clip-controller interface with respect to clip arm 32a (e.g., by using clip controller 36).

For some applications of the invention, at least one of clip arms 32 comprises or defines grips 38 and/or teeth 40, which are configured to facilitate coupling of clip 30 to a native leaflet of the native valve. Typically, grips 38 are configured to atraumatically grip the leaflet and teeth 40 are configured to grip, fold around, and/or pierce the leaflet. For some applications of the invention, at least a portion of clip arms 32 is covered with a padding (not shown), configured to cushion the contact between the clip arms and the leaflet.

Typically, clip 30 is lockable, such that clip arm 32b is locked (e.g., immobile) with respect to clip arm 32a. FIGS. 1B-D show clip 30 comprising a locking element 50 (e.g., a securing element), which facilitates locking of the clip. Locking element 50 typically comprises at least one ratchet mechanism 52, comprising (1) a rack 51, comprising a plurality of sockets 54, and (2) an engaging element 56 (e.g., a pawl, or a tooth). Typically, rack 51 is defined by, or is fixedly coupled to, clip arm 32a, and engaging element 56 is coupled to, or defined by, clip-controller interface 34. However, the scope of the invention includes other (e.g., inverse) arrangements of ratchet mechanism 52.

FIG. 1B shows clip 30 in an unlocked configuration thereof, in which an obstructing element 58 (e.g., a restraint) is disposed between rack 51 and engaging element 56, thereby inhibiting (e.g., obstructing) engaging element 56 from engaging rack 51, and thereby facilitating the opening and closing of the clip (i.e., movement between open and closed states thereof). Typically, obstructing element 58 is integral with delivery apparatus that is used to deliver support 22 to the native valve (e.g., delivery apparatus 140, described hereinbelow with reference to FIGS. 3A-D). FIG. 1B shows a front view and a back view of clip 30 in the open state thereof, and a front view and a back view of the clip in the closed state thereof.

FIG. 1C shows a back view of clip 30 in a locked configuration thereof, in which obstructing element 58 has been removed from between rack 51 and engaging element 56 (e.g., by withdrawing the obstructing element proximally), and an engaging element 56 has engaged the rack. Typically, element 56 is configured (e.g., shape-set) to automatically engage rack 51 upon removal of obstructing element 58.

For some applications, and as shown in FIGS. 1B-D, obstructing element 58 comprises a longitudinal member, such as a strip or rod, and is removed by being withdrawn proximally. However, obstructing element 58 may have other shapes and/or shape-memory features that facilitate the obstruction of engaging element 56 and/or the removal of the obstructing element. For example, obstructing element 58 may have a generally circular, rectangular, triangular, or hexagonal cross-section, and/or may be shape-set to facilitate removal thereof, and thereby to facilitate locking of the clip.

For some applications of the invention, and as shown in FIGS. 1B-D, locking element 50 comprises two ratchet mechanisms 52. The two ratchet mechanisms are offset with respect to the other, such that at a position of clip-controller interface 34 in which the engaging element 56 of one ratchet mechanism is fully disposed in a socket 54, the engaging element of the other ratchet mechanism is not fully disposed in a socket of the other rack (FIGS. 1C-D). This configuration increases (e.g., doubles) the number of positions within a given range in which clip-controller interface 34 is lockable, without reducing the size of each socket 54. That is, this configuration increases the "resolution" or "density" of locking positions of dip 30. It is hypothesized that, for some applications, it is advantageous to combine this configuration of locking element 50 with the lever-like clip-controller interface described hereinabove, such that the relatively large movement of clip arm 32b is at least partly offset by the "high resolution" of the locking element, thereby increasing the degree of control that the physician has on the clip.

As described hereinabove, clip-controller interface 34 is typically reversibly couplable to clip controller 36. Typically, this reversible coupling is facilitated by a projection 42, defined by clip controller 36, which is configured to be disposed within, and removed from, a depression 44, defined by clip-controller interface 34. Further typically, projection 42 is configured (e.g., shape-set) to move out from depression 44, and is prevented from moving out of depression 44 by obstructing element 58. Following the locking of dip 30 by withdrawing obstructing element 58 (FIG. 1C), the obstructing element is further withdrawn (FIG. 1D), thereby releasing projection 42 from depression 44, and thereby decoupling clip controller 36 from clip-controller interface 34. Clip 30 is typically configured such that the physician may repeatedly lock and unlock clip 30 (e.g., by partially withdrawing and replacing obstructing element 58) before finally decoupling the controller (e.g., by completely withdrawing obstructing element 58), such as after confirming that clip 30 has been successfully coupled to the native leaflet.

As described hereinabove, clips 30 are typically configured to be controllable (i.e., openable and closable) independently of each other, and/or independently of deployment of prosthetic valve support 22. Clips 30 are further typically lockable and/or decouplable from controller 36 independently of each other, and/or independently of deployment of the prosthetic valve support. It is to be noted that clips 30 are configured to couple the prosthetic valve support to the native leaflets suturelessly.

Referring again to FIG. 1A, prosthetic valve support 22 typically comprises a generally annular upstream support portion 60 (e.g., an annular portion), shaped to define an opening 61 (e.g., an aperture) therethrough, and to be placed against an upstream side of the native valve. Typically, upstream support portion 60 comprises an expandable lattice-structure frame 62 (e.g., comprising a plurality of struts), covered by a covering 64. Opening 61 is defined by an inner perimeter 68 of the prosthetic valve support. For some applications, frame 62 defines a plurality of barbs 67 that protrude radially inwardly from inner perimeter 68, and facilitate coupling of a prosthetic valve to the prosthetic valve support (e.g., as described hereinbelow with reference to FIGS. 3H-I).

Upstream support portion 60 typically has shape-memory (e.g., resilient, pseudoelastic and/or superelastic) properties. Typically, frame 62 comprises a shape-memory (e.g., resilient, pseudoelastic and/or superelastic) material, such that upstream support portion 60 is compressible (e.g., crimpable) when a compressive force is applied (e.g., prior to implantation), and re-expandable when the compressive force is removed (e.g., during implantation). Non-limiting examples of materials that frame 62 may comprise, include nickel-titanium (nitinol), stainless steel, nickel cobalt, cobalt chrome, titanium, tantalum, and palladium.

Non-limiting examples of materials that covering 64 may comprise, include polyethylene terephthalate (e.g., polyester), polytetrafluoroethylene (e.g., Teflon, ePTFE), and pericardial tissue. For some applications, covering 64 comprises a fabric. Typically, a thickness of the covering is less than 0.5 mm, such as less than 0.2 mm, e.g., less than 0.1 mm, or less than 0.05 mm.

FIG. 1A shows upstream support portion 60 in an expanded (e.g., fully uncompressed and/or deployed) configuration thereof, in which upstream support portion 60 (i.e., an outer perimeter 69 thereof) typically has a diameter d3 that is greater than 40 mm and/or less than 80 mm (e.g., 40-80 mm, such as 40-70 mm, such as 40-60 mm). That is, an outer diameter of upstream support portion 60 is typically greater than 40 mm and/or less than 80 mm (e.g., 40-80 mm, such as 40-70 mm, such as 40-60 mm). Opening 61, defined by inner perimeter 68, typically has a diameter d4 of greater than 20 mm and/or less than 35 mm (e.g., 20-35 mm, such as 23-32 mm, such as 25-30 mm). That is, an inner diameter of upstream support portion 60 is typically greater than 20 mm and/or less than 35 mm (e.g., 20-35 mm, such as 23-32 mm, such as 25-30 mm). Typically, diameter d3 is at least 10% (e.g., at least 50%, such as at least 80%) greater than diameter d4.

Figure 3B:
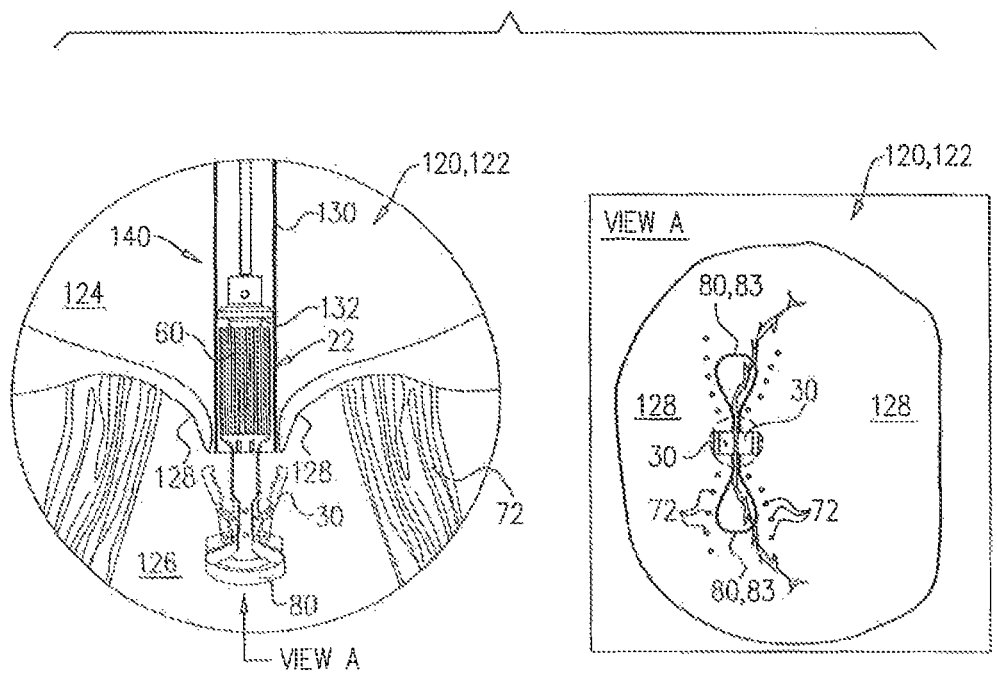

Upstream support portion 60 is typically compressible (e.g., crimpable; for delivery to the native valve) into a generally cylindrical shape in which inner perimeter 68 defines a downstream end 71 of the cylindrical shape, and outer perimeter 69 defines an upstream end 73 of the cylindrical shape (see FIG. 3A). Typically, the generally cylindrical shape of upstream support portion 60 has a transverse cross-sectional diameter (e.g., a width) of greater than 3 mm and/or less than 9 mm (e.g., 3-9 mm, such as 5-8 mm, such as 6-7 mm), and a height, from the upstream end to the downstream end, of greater than 11 mm and/or less than 30 mm (e.g., 11-30 mm, such as 15-30 mm, such as 15-25 mm).

In the expanded configuration thereof, upstream support portion 60 is typically (but not necessarily) generally flat (e.g., laminar, and/or planar). For some applications, in the expanded configuration, upstream support portion 60 assumes a frustoconical shape. Upstream support portion 60 typically has a thickness of less than 5 mm, e.g., less than 2 mm, such as between 0.3 mm and 2 mm. Inner perimeter 68 (and thereby opening 61) thereby typically has a depth d10 (e.g., a height) from an upstream side 59 of the upstream support portion to a downstream side 63 of the upstream support portion. Depth d10 is less than 5 mm, e.g., less than 2 mm, such as between 0.3 mm and 2 mm. Typically, diameter d4 of opening 61 is more than 4 times (e.g., more than 6 times, such as more than 10 times) greater than depth d10. That is, opening 61 is more than 4 times (e.g., more than 6 times, such as more than 10 times) wider than it is deep. Typically, in the expanded configuration, upstream support portion 60 has a total height of less than 10 mm (e.g., less than 5 mm, such as less than 2 mm).

Typically, inner perimeter 68 comprises, or is defined by, a free inner edge of upstream support portion 60. That is, opening 61 resembles a hole cut out of a lamina (e.g., out of a disc). For some applications, inner perimeter 68 comprises, or is defined by, a curved and/or folded inner edge of upstream support portion 60. If the inner perimeter of upstream support portion 60 comprises, or is defined by, a curved or folded edge, then a radius of curvature of the curved or folded edge is typically less than 2.5 mm, such as less than 1 mm. That is, the curve or fold of the edge is generally sharp, such that when viewed from within opening 61, the curved or folded edge looks generally like a free edge.

Prosthetic valve support 22 typically comprises two or more tissue-engaging elements 24 (e.g., clips 30), coupled to inner perimeter 68 of upstream support portion 60. For such applications, the two tissue-engaging elements are typically disposed opposite each other (e.g., at 180 degrees around inner perimeter 68 from each other).

Typically, tissue-engaging elements 24 (e.g., clips 30) are coupled to upstream support portion 60 (e.g., inner perimeter 68 thereof) by a flexible connector 70, which may comprise polyethylene terephthalate (e.g., polyester), polytetrafluoroethylene (e.g., Teflon, ePTFE), a fabric, nitinol, and/or any other suitable material. Thereby, tissue-engaging elements 24 (e.g., clips 30) are typically flexibly coupled to upstream support portion 60, and/or are able to move independently of each other. Connector 70 may be coupled to upstream support portion 60 and tissue-engaging elements 24 using sutures, welding, and/or any other suitable technique known in the art.

Prosthetic valve support 22 typically further comprises a stabilizing element 80, coupled to clips 30 (e.g., to a downstream portion thereof). Typically, stabilizing element 80 forms a ring shape that defines an opening 81 (e.g., an aperture), and is typically inelastic and at least partly flexible. Opening 81 typically, but not necessarily, has a diameter that is generally equal to diameter d4 of opening 61. Non-limiting examples of materials that stabilizing element 80 may comprise include polyethylene terephthalate (e.g., polyester), PTFE (e.g., ePTFE), nylon, cotton, nitinol, stainless steel, nickel cobalt, cobalt chrome, titanium, tantalum and palladium. Typically, and as shown in FIG. 1A, stabilizing element 80 comprises (1) an outer coat 82 of a flexible material (e.g., polyester), which typically provides inelasticity, and (2) an inner strip 84 of a shape-memory material (e.g., nitinol), which is typically configured (e.g., shape-set) to bias element 80 to assume a ring-shaped configuration.

Stabilizing element 80 (and thereby opening 81) typically has a depth d11 (e.g., a height from a most upstream part to a most downstream part) of less than 20 mm (e.g., less than 10 mm, e.g., less than 5 mm, such as less than 1 mm). As described hereinabove, inner perimeter 68 of upstream support portion has a depth d10 of less than 5 mm. Typically, in the expanded configuration, no part of prosthetic valve support 22 that circumscribes a space that has a perimeter greater than 60 mm (e.g., as upstream support portion 60 and stabilizing element 80 typically do) has a height of more than 20 mm. For some applications, in the expanded configuration, no part of the support that circumscribes a space that has a perimeter greater than 60 mm has a height of more than 10 mm. For some applications, in the expanded configuration, no part of the support that circumscribes a space that has a perimeter greater than 60 mm has a height of more than 5 mm.

Reference is made to FIGS. 2A-D, which are schematic illustrations of prosthetic valve support 22 and/or components thereof, in accordance with respective applications of the invention. As described hereinabove, upstream support portion 60 is generally annular. For some applications, and as shown in FIG. 1A, upstream support portion 60 has a generally circular outer perimeter 69. FIG. 2A shows an alternative embodiment in which upstream support portion 60 comprises an upstream support portion 90, which has a non-circular outer perimeter 99. FIG. 2A shows outer perimeter 99 as generally oval, with a "squashed" portion 92. Such a configuration may, for example, facilitate placement of upstream support portion 90 at a mitral valve of the subject, with squashed portion 92 facing the interatrial septum. It is to be noted, that the scope of the invention includes upstream support portions having other shapes, configured according to the anatomical site at which they are to be placed. For example, for some applications, upstream support portion 60 and/or upstream support portion 90 may have radially-protruding bulges or wings (not shown), configured to stabilize the upstream support portion and/or to inhibit leakage between the native valve and the upstream support portion.

As described hereinabove, upstream support portion 60 typically comprises an expandable lattice-structure frame 62. FIG. 2B shows an alternative embodiment in which to upstream support portion 60 comprises a braided upstream support portion 100, which comprises a braided structure of intertwining strands 102, at least some of which are slidable past (e.g., over, under) each other. Typically, strands 102 comprise a shape-memory material such as, but not limited to, nitinol. Upstream support portion 100 is transluminally deliverable in a compressed configuration, and is expandable to an annular, expanded configuration at the native valve. Typically, support 100 is configured to automatically expand to the expanded configuration, and this expansion is controlled by progressively releasing (e.g., loosening and/or unthreading) a restricting element 104 (e.g., a drawstring), which, when threaded through parts of upstream support portion 100 (e.g., one or more rings 106 thereof), is configured to restrict expansion of the upstream support portion (e.g., to retain the upstream support portion in the compressed configuration thereof). FIG. 2B shows sequential stages in the deployment of upstream support portion 100 from a delivery tube 108. Typically, upstream support portion 100 is recompressible by tightening (e.g., pulling) the restricting element.

As described hereinabove, prosthetic valve support 22 comprises one or more tissue-engaging elements 24, and typically further comprises upstream support portion 60 and/or stabilizing element 80. FIG. 1A shows prosthetic valve support 22 comprising both upstream support portion 60 and stabilizing element 80. FIG. 2C shows an alternative embodiment in which prosthetic valve support 22 comprises a prosthetic valve support 322, which does not comprise stabilizing element 80. FIG. 2D shows an alternative embodiment in which prosthetic valve support 22 comprises a prosthetic valve support 422, which does not comprise an upstream support portion (e.g., upstream support portion 60). For some applications of the invention, when implanted at the native valve, no portion of prosthetic valve support 422 is disposed upstream of the native annulus.

It is to be noted that upstream support portions 90 and 100, and prosthetic valve supports 322 and 422, may be used (e.g., combined) with apparatus and methods described elsewhere herein. For example, the upstream support portion of any of the prosthetic valve supports described herein may be replaced with upstream support portion 90 or upstream support portion 100, resulting in alternative prosthetic valve supports. Furthermore, these resulting prosthetic valve supports, as well as prosthetic valve supports 322 and 422, may be used in combination with other techniques described herein (e.g., with reference to FIGS. 3A-I, 4A-F, 5, 6A-B, 7, 8, and/or 9A-C), mutatis mutandis.

Reference is made to FIGS. 3A-I, which are schematic illustrations of steps in the delivery and implantation of prosthetic valve support 22 at a native heart valve 120 of heart 250 of a subject, and the use thereof to facilitate implantation of a prosthetic valve 150, in accordance with some applications of the invention. FIGS. 3A-I show native valve 120 as comprising a mitral valve 122 of the subject, but it is to be noted that the scope of the invention includes the use of prosthetic valve support 22 at other heart valves of the subject.

Mitral valve 122 is disposed between a left atrium 124 and a left ventricle 126 of the subject, and comprises two leaflets 128. Atrium 124 is upstream of mitral valve 122 and ventricle 126 is downstream of the mitral valve. Prosthetic valve support 22, in a compressed configuration thereof, is advanced transluminally (e.g., transfemorally and/or transseptally) within a delivery tube 130 of delivery apparatus 140, to atrium 124, and between leaflets 128 (FIG. 3A).

Prosthetic valve support 22 is advanced out of delivery tube 130 and/or the delivery tube is withdrawn from the prosthetic valve support (FIG. 3B). Clips 30 (and/or other tissue-engaging elements) are typically disposed at a downstream portion of prosthetic valve support 22 (e.g., downstream of downstream end 71 of upstream support portion 60) in the compressed configuration thereof, and are thereby exposed from delivery tube 130. Stabilizing element 80 is also typically exposed from the delivery tube, and typically forms a generally lemniscate (e.g., FIG. 8) shape, defining two "loops" 83. Typically, the axis between loops 83 of the lemniscate is generally orthogonal to the axis between clips 30, and may be used to orient prosthetic valve support 22, e.g., such that clips 30 point toward leaflets 128 of the native valve. For example, loops 83 may be disposed between chordae tendineae 72 of one leaflet and those of the other leaflet, and physical contact between the chordae tendineae and the loops automatically and/or via tactile feedback to the physician, facilitates orientation of the prosthetic valve support. Alternatively or additionally, the lemniscate shape of stabilizing element 80 may be visualized using imaging techniques such as fluoroscopy and/or ultrasound. Clips 30 are opened (e.g., as described hereinabove with reference to FIG. 1B).

Prosthetic valve support 60 is moved upstream (e.g., proximally) so as to envelope leaflets 128 between clip arms 32 of each clip 30, and each clip is closed around a leaflet, thereby coupling each clip to a leaflet, e.g., by clamping the leaflet between the clip arms (FIG. 3C). Each clip 30 couples to a single leaflet 128, such that one clip arm of each clip (e.g., clip arm 32a) engages an upstream surface of the leaflet (e.g., an upstream side of the leaflet), and the other clip arm of each clip (e.g., clip arm 32b) engages a downstream surface of the leaflet (e.g., a downstream side of the leaflet). Although each clip typically couples to only one leaflet, for some applications, more than one clip couples to each leaflet.

As described hereinabove, clips 30 (and/or other tissue-engaging elements 24) are typically coupled to the leaflets of the native valve before prosthetic valve support 22 is fully deployed. Clips 30 are typically locked (e.g., as described with reference to FIG. 1C), and subsequently decoupled from clip controller 36 (e.g., as described with reference to FIG. 1D). FIGS. 3C-F show stages in the deployment of prosthetic valve support 22 (e.g., of upstream support portion 60 thereof). Upstream support portion 60 typically progressively expands as it is exposed from delivery tube 130. Thereby, typically, (1) downstream end 71 of the cylindrical shape of the upstream support portion in the compressed configuration thereof, expands to become inner perimeter 68 of the upstream support portion in the expanded configuration thereof, and (2) subsequently, upstream end 73 of the cylindrical shape expands to become outer perimeter 69 of the upstream support portion.

Delivery apparatus 140 typically comprises a pushing member 132. Typically, prosthetic valve support 22 (e.g., upstream support portion 60 thereof) is reversibly coupled to pushing member 132, and is exposed from delivery tube 130 by being pushed using the pushing member. Upstream support portion 60 is typically configured (e.g., shape-set) to automatically expand toward its expanded configuration upon being deployed from delivery tube 130. For some applications of the invention, the upstream support portion "pops" open from the configuration shown in FIG. 3C to the configuration shown in FIG. 3F, immediately upon exposure of upstream end 73 of the upstream support portion from delivery tube 130.

For some applications, and as shown in FIGS. 3C-F, one or more holding members 134, coupled to, and decouplable from, upstream support portion 60, facilitate controlled expansion of the upstream support portion. For example, holding members 134 may be configured to allow a physician (1) to expand some portions of the upstream support portion before other portions and/or (2) to adjust the positioning of the upstream support portion on the upstream surface of the native valve following expansion of the upstream support portion. For some applications, two holding members 134 are used, and are coupled to opposite sides of upstream support portion 60 to each other (e.g., 180 degrees around the upstream support portion from each other).

For some applications, and as shown in FIGS. 3D-F, three holding members 134 are used. For such applications, each holding member 134 is coupled at between 90 and 180 degrees (e.g., between 100 and 150 degrees, such as at 120 degrees) around the upstream support portion from the other holding members. For some such applications, and as shown in FIG. 3F, the holding members are coupled to the upstream support portion such that, when the upstream support portion is positioned at the native valve, two holding members are disposed generally above respective commissures of the native valve, and the third holding member is disposed generally midway around posterior leaflet 128p of the native valve.

For some applications, holding members 134 comprise locking elements and/or coupling leads (e.g., coupling wires, e.g., looped around respective portions of the upstream support portion; not shown in FIGS. 3D-F) that couple the holding members to the upstream support portion, and the holding members are decoupled from the upstream support portion by unlocking the locking elements and/or unlooping the loops. For some applications of the invention, holding members 134 also facilitate retrieval of the upstream support portion, and thereby of prosthetic valve support 22, e.g., as described with reference to FIGS. 4A-F.

FIG. 3G shows prosthetic valve support 22 following coupling, deployment and expansion (i.e., implantation) thereof at mitral valve 122, and withdrawal of delivery apparatus 140. As described hereinabove, prosthetic valve support 22 is configured to be coupled to the native heart valve (e.g., to leaflets thereof) without eliminating check valve functionality of the native heart valve. Typically, and as shown in FIG. 3G, clips 30 couple the prosthetic valve support to leaflets 128 such that (1) the leaflets define a single orifice, and (2) the native valve functions as a single check valve (e.g., functions in a manner that is generally similar to the natural (e.g., physiological) function of the native valve). Stabilizing element 80 is also configured to allow such movement of leaflets 128. e.g., the stabilizing element is sufficiently flexible to flex in response to the leaflets moving in response to pumping of the heart. FIG. 3G shows (1) in solid, mitral valve 122 (e.g., leaflets 128) closed, and the respective state of prosthetic valve support 22, and (2) in phantom, the mitral valve (e.g., the leaflets) open, and the respective state of the prosthetic valve support.

Thereby, when prosthetic valve support 22 is implanted at an atrioventricular valve of the subject (e.g., mitral valve 122 or a tricuspid valve), clips 30 typically move away from each other during ventricular diastole, and toward each other during ventricular systole. For applications in which prosthetic valve support 22 is implanted at a native semilunar valve of the subject (e.g., an aortic valve or a pulmonary valve), clips 30 typically move toward each other during ventricular diastole, and away from each other during ventricular systole.

Subsequently (e.g., immediately subsequently, or after more than a minute, e.g., after more than 2 minutes, e.g., after more than 5 minutes, such as after more than an hour), a prosthetic valve 150 is transluminally delivered, in a compressed configuration thereof (e.g., within a delivery tube 160), to the native valve, and implanted at the native valve by coupling the prosthetic valve to prosthetic valve support 22. Implantation of prosthetic valve 150 replaces check valve functionality of the native valve with a substitute check valve functionality of the prosthetic valve. The substitute check valve functionality is provided by one or more prosthetic check valve elements (e.g., valve members, such as leaflets, a ball, or a disc), such as those known in the art, which the prosthetic valve comprises (not shown).

Typically, and as shown in FIG. 3H, respective portions of prosthetic valve 150 are placed within opening 61 (defined by upstream support portion 60) and/or opening 81 (defined by stabilizing element 80), and are expanded such that the respective portions engage the upstream support portion and the stabilizing element, respectively. Typically, prosthetic valve 150 is configured to automatically expand upon deployment from delivery tube 160, and radially-expansive force applied by prosthetic valve 150 to upstream support portion 60 and/or stabilizing element 80 facilitates coupling of the prosthetic valve to prosthetic valve support 22.

FIG. 3I shows prosthetic valve 150 having been fully deployed and coupled to prosthetic valve support 22. That is, FIG. 3I shows an implant 180, comprising prosthetic valve support 22 and prosthetic valve 150, having been implanted at native valve 120 (e.g., at mitral valve 122). Prosthetic valve 150 is described in more detail hereinbelow.

Typically, diameter d3 of upstream support portion 60 is greater than a diameter d5 of the native valve (e.g., a diameter of the orifice of the native valve, e.g., an inner diameter of the annulus of the native valve). Further typically, diameter d4 of opening 61 is smaller than diameter d5. When prosthetic valve 150 is expanded within opening 61 of the upstream support portion, a diameter d6 of the prosthetic valve is typically restricted by the upstream support portion to the same diameter as diameter d4 of opening 61. For some applications, contact between prosthetic valve 150 and upstream support portion 60 (e.g., resulting from the radially-expansive force of the valve on the support) couples the prosthetic valve to the prosthetic valve support, and/or inhibits retrograde leakage of blood therebetween.

When implanted at the native valve (e.g., when in respective expanded configurations), a height d9 of prosthetic valve 150 is typically at least 1.5 times greater (e.g., at least 3 times greater, such as at least 5 times greater) than the total height of upstream support portion 60. Typically, height d9 is at least 1.5 times greater (e.g., at least 3 times greater, such as at least 5 times greater) than depth d10 of opening 61.

As described hereinabove, upstream support portion 60 is configured to be placed against an upstream side of the native valve. It should be noted, that radial expansion of prosthetic valve 150 against inner perimeter 68 of upstream support portion 60, thereby typically does not cause the prosthetic valve support to apply a radially-expansive force to the native valve annulus. For some applications of the invention, this expansion of prosthetic valve 150 does not cause the prosthetic valve support to apply the radially-expansive force to the native valve annulus because no part of the prosthetic valve support that circumscribes the prosthetic valve is sandwiched between the prosthetic valve and the native valve annulus.

For some applications, prosthetic valve 150 is couplable to upstream support portion 60 at a plurality of positions along the length of the prosthetic valve. That is, a physician can couple the prosthetic valve at a plurality of depths within the support. For some applications, the prosthetic valve is couplable to the upstream support portion at a continuum of positions along the length of the prosthetic valve. That is, a physician can couple the prosthetic valve to the support at a continuum of depths within the support. For example, in some applications in which the prosthetic valve is configured to be coupled to the upstream support portion solely by the radially-expansive force, the prosthetic valve may be coupled to the upstream support portion at a continuum of positions along the length of the prosthetic valve.

For some applications, sealing between implant 180 and native valve 120 is facilitated by native leaflets 128 being pushed closed against the outer surface of the frame of the valve during systole, in a manner similar to that in which native valve leaflets of a healthy native valve coapt during systole.

For applications in which diameters d4 and d6 are relatively large, the proportion (e.g., the surface area) of the native leaflets that is pushed against the outer surface of the valve during systole is relatively large, thereby enhancing the sealing of the native leaflets with respect to the frame of the prosthetic valve. However, for some applications, beyond a given size, as diameters d4 and d6 increase, the native valve leaflets are pushed apart at the commissures, thereby potentially increasing a likelihood of paravalvular retrograde leakage of blood at the commissures. Therefore, for some applications of the present invention, prosthetic valve support 22 (and, typically, prosthetic valve 150) are selected such that diameters d4 and d6 are less than 90% (e.g., 5 less than 80%, e.g., less than 60%, such as less than 50%) of diameter d5 of the native valve (e.g., of the orifice of the native valve). Thus prosthetic valve support 22 facilitates sealing of the prosthetic valve with respect to the native valve, by facilitating closing of the native valve leaflets around the outer surface of the prosthetic valve.

In experiments conducted by the inventors, a prosthetic valve support 22 was implanted in two pigs. Both animals remained alive and stable (e.g., were hemodynamically stable, and had stable breathing rate and oxygen saturation) for a duration of sufficient length to withdraw delivery apparatus 140, introduce a valve-delivery system, and deploy (e.g., implant) a prosthetic valve in opening 61 of the support. The period between implanting prosthetic valve support 22 and implanting the prosthetic valve was between 5 and 10 minutes. During this duration, the native valve of the animals functioned generally normally. For example, native leaflet movement and coaptation, and blood flow therebetween was generally normal during this duration.

It is thereby hypothesized that, following implantation of prosthetic valve support 22, the heart of the subject is able to continue pumping blood sufficiently to support the subject (e.g., to maintain hemodynamic stability) for longer than a minute, e.g., longer than 2 minutes, e.g., longer than 5 minutes, such as longer than an hour. It is thereby hypothesized that a period of generally normal physiological activity of the subject of up to a minute, e.g., up to 2 minutes, e.g., up to 5 minutes, such as up to an hour, between implantation of prosthetic valve support 22 and implantation of a prosthetic valve (e.g., prosthetic valve 150) is supported by prosthetic valve support 22. It is thereby hypothesized that, for some applications, the implantation of implant 180 may be performed without the use of cardiopulmonary bypass. It is thereby further hypothesized that replacement of a native valve with implant 180, may, for some applications, be performed in a human, "off-pump," as was performed in the pig experiments.

Reference is again made to FIG. 3I. For some applications of the invention, the prosthetic valve that is expanded within, and coupled to, prosthetic valve support 22, comprises a generally cylindrical prosthetic valve. For some applications, the prosthetic valve comprises a prior art prosthetic valve, e.g., a currently commercially-available prosthetic valve. That is, for some applications, prosthetic valve support 22 may be used to facilitate implantation of a prior art prosthetic valve, such as a currently commercially-available prosthetic valve. For some applications, and as shown in FIG. 3I, the prosthetic valve comprises prosthetic valve 150, which comprises (1) a generally cylindrical valve body 152 (e.g., a primary structural element), within which one or more prosthetic check valve elements (e.g., valve members, such as leaflets, a ball, or a disc) are disposed (not shown), and (2) one or more valve-anchoring elements 154 which protrude (e.g., radially) from the valve body. Typically, valve-anchoring elements 154 are disposed at a downstream end of prosthetic valve 150 (e.g., at a downstream end of valve body 152), and protrude outward and upstream. For some applications, and as shown in FIG. 3I, valve-anchoring elements 154 fold back toward valve body 152, and are configured to sandwich stabilizing element 80, clips 30 and/or native leaflets 128 between the valve-anchoring elements and the valve body. For some applications, prosthetic valve 150 does not comprise valve-anchoring elements 154.

As described hereinabove, coupling of prosthetic valve 150 to prosthetic valve support 22 is typically facilitated by radially-expansive force applied by the valve to the support. Typically, prosthetic valve 150 comprises an expandable lattice-structure frame 151 (e.g., comprising a plurality of struts). For applications of the invention in which upstream support portion 60 comprises inwardly-protruding barbs 67 (e.g., as shown in FIGS. 1A and 2A), the barbs protrude into frame 151 (e.g., between struts thereof), thereby further facilitating coupling of the prosthetic valve to the prosthetic valve support.

Typically, at least portions of the inner surface of prosthetic valve 150 (e.g., of valve body 152) are covered with a covering 156, to facilitate channeling of blood through the valve body, as is known in the art. That is, at least portions of prosthetic valve 150 (e.g., of valve body 152) are lined with covering 156. Covering 156 may comprise the same material(s) as covering 64 described hereinabove, and/or may comprise other materials.

For some applications, an upstream portion of prosthetic valve 150 (e.g., of valve body 152) alternatively or additionally comprises a netting 158, which facilitates coupling of the prosthetic valve to prosthetic valve support 22. Netting 158 may be disposed on the inner surface and/or the outer surface of the upstream portion of the prosthetic valve (e.g., of valve body 152), and/or between the struts of frame 151. Typically, netting 158 is disposed upstream of a point at which leaflets 182 contact (e.g., seal around) valve body 152.

Typically, netting 158 facilitates coupling of prosthetic valve 150 to prosthetic valve support 22 by providing a higher-resolution lattice through which barbs 67 of the prosthetic valve support are configured to protrude. Netting 158 may additionally insulate respective metallic surfaces of the prosthetic valve and the prosthetic valve support (e.g., of frames 62 and 151) from each other. It is hypothesized that this insulation reduces fatigue, corrosion, chipping and/or wear of the metallic surfaces, and/or electrostatic discharge between the metallic surfaces.

For some applications, a material that inhibits (e.g., prevents) tissue growth (e.g., polytetrafluoroethylene (PTFE), and/or pericardium) may be disposed on a surface of prosthetic valve 150 and/or prosthetic valve support 22 (e.g., clips 30 thereof). Alternatively or additionally, a material that facilitates (e.g., enhances) tissue growth (such as polyethylene terephthalate; PET) may be disposed on a surface of the prosthetic valve and/or the prosthetic valve support (e.g., clips 30 thereof), in order to facilitate sealing and/or coupling to the native valve.

It is hypothesized that the use of prosthetic valve support 22 advantageously facilitates delivery of a prosthetic valve via a catheter narrower than 28 Fr (i.e., less than 9.3 mm), e.g., narrower than 24 Pr (i.e., less than 8 mm), such as by allowing the use of a "minimalistic" prosthetic valve, comprising a generally cylindrical valve body, and valve members (e.g., leaflets) disposed therein, and comprising few or no other components and/or appendages. Typically, prosthetic valve support 22 is also delivered via a similarly narrow catheter, e.g., via the same catheter. The use of such a narrow catheter advantageously facilitates transluminal (e.g., transfemoral) delivery and implantation of the prosthetic valve and prosthetic valve support.

It is to be noted that, although FIGS. 3A-I show prosthetic valve support 22 being implanted and used to facilitate implantation of a prosthetic valve, the techniques described may be applied to other prosthetic valve supports described herean (e.g., prosthetic valve supports 220, 322, 422 and 522), mutatis mutandis.

Reference is made to FIGS. 4A-F, which are schematic illustrations of a system 200 for facilitating controlled expansion and/or retrievability of upstream support portion 60, in accordance with some applications of the invention. System 200 comprises one or more holding members 134, reversibly coupled to upstream support portion 60 by one or more coupling leads 202 (e.g., coupling wires). Typically, two or more (e.g., three) holding members are coupled to the upstream support portion via two or more (e.g., three) coupling leads. Typically, the ends of each coupling lead 202 are disposed within holding members 134, or more proximally (e.g., outside a body of the subject). Coupling leads 202 may comprise metallic wire, suture, or any other suitable material.

A portion (e.g., a middle portion) of each coupling lead 202 is disposed within (e.g., threaded and/or looped through) a respective portion of upstream support portion 60, thereby coupling the upstream support portion to holding members 134. Typically, this middle portion of each coupling lead is disposed through a peripheral region (e.g., close to an outer edge 69) of the prosthetic valve support.

Figure 4A:
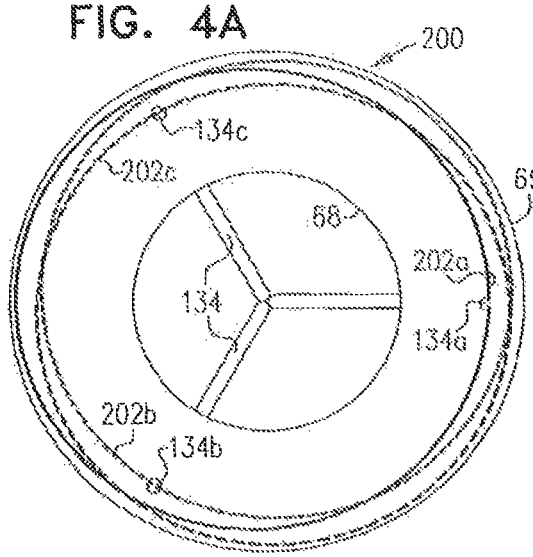
FIGS. 4A-F are schematic illustrations of a system for facilitating controlled expansion and/or retrievability of an upstream support portion of the prosthetic valve support, in accordance with some applications of the invention.

For example, and as shown in FIG. 4A, three coupling leads 202 (e.g., coupling leads 202a, 202b, and 202c) couple three respective holding members 134 (e.g., holding members 134a, 134b and 134c) to upstream support portion 60. One end of each coupling lead 202 extends from a respective holding member 134, passes around (e.g., is looped and/or threaded through) upstream support portion 60, and returns to the same holding member. Thereby, each coupling lead is configured to apply a respective annular pulling force to the entire upstream support portion, when the coupling lead is pulled.

Figure 4B:
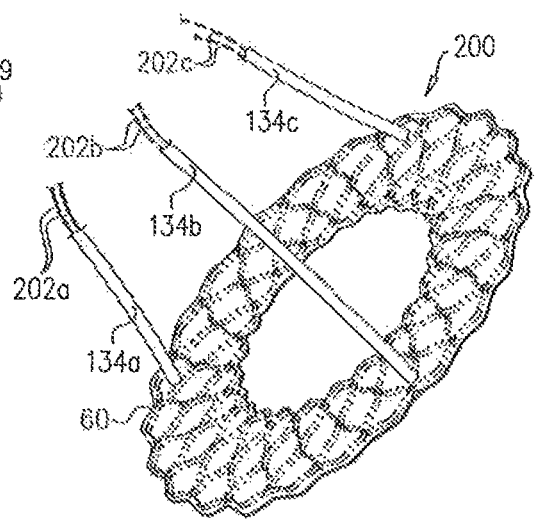
Figure 4C:
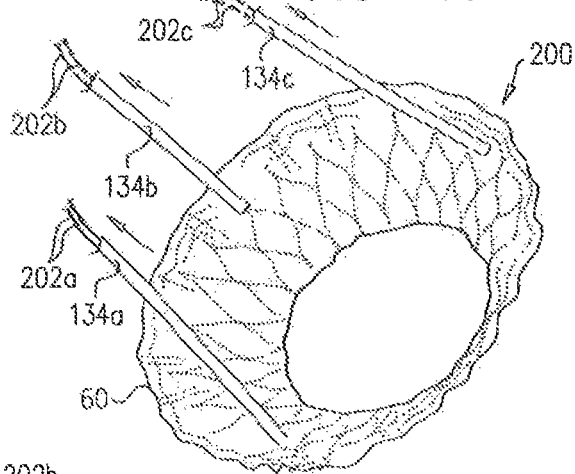
Figure 4D:
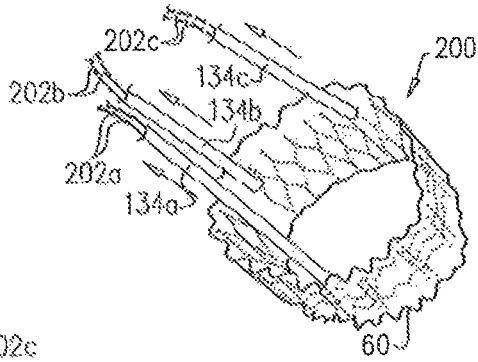
Figure 4E:
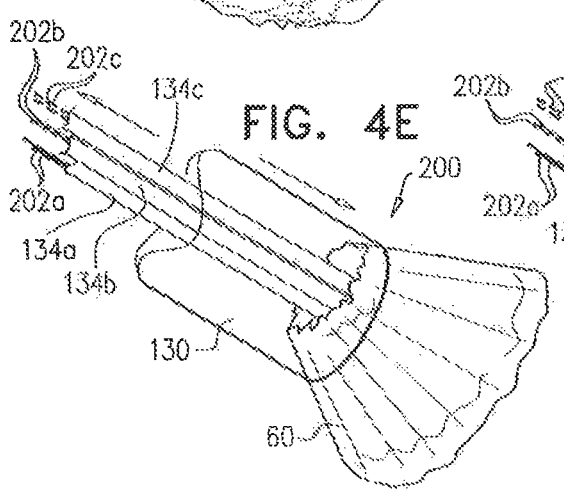
Figure 4F:
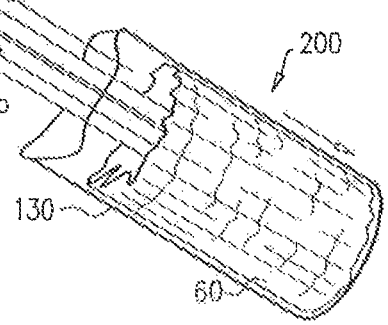

For some applications of the invention, system 200 is configured to facilitate transluminal retrieval of upstream support portion 60 following expansion of the upstream support portion at the native valve. Upstream support portion 60 is deployed at the native valve, e.g., as described with reference to FIGS. 3C-F, mutatis mutandis. Should it be desirable and/or necessary to retrieve upstream support portion 60 into delivery tube 130, and/or to remove the upstream support portion entirely from the subject, pulling of coupling leads 202 recompresses upstream support portion 60 into a generally cylindrical configuration, e.g., toward and/or into the compressed delivery configuration thereof (FIGS. 4B-D). Subsequently, upstream support portion 60 may be withdrawn into delivery tube 130 (FIGS. 4E-F).

System 200 may alternatively or additionally be configured to facilitate controlled expansion of upstream support portion 60. During deployment of upstream support portion 60, coupling leads 202 are gradually released (e.g., fed distally). This technique may be understood by considering FIGS. 4B-F in reverse order, mutatis mutandis. Thereby, the rate of expansion of upstream support portion 60 is controllable. Alternative configurations and/or arrangements of coupling leads 202 may be used, e.g., to facilitate controlled expansion of different portions of upstream support portion 60.

It is to be noted that the techniques described with reference to FIGS. 4A-F may be used in combination with other upstream support portions described herein (e.g., upstream support portions 90 and 100), mutatis mutandis.

Figure 5:
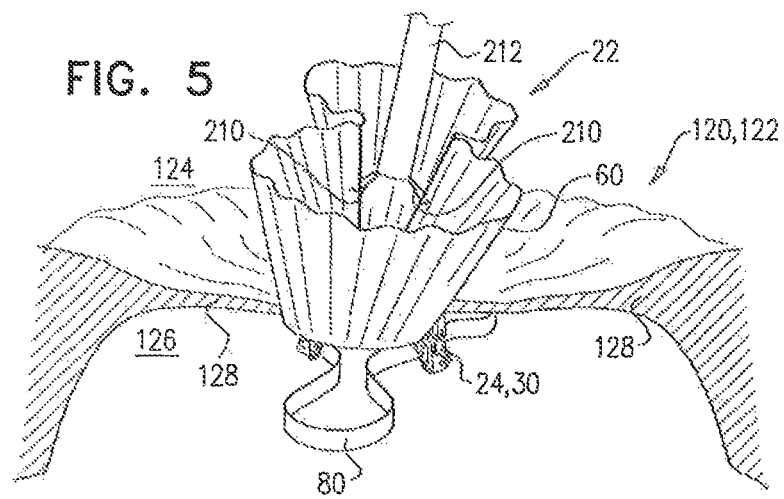
FIG. 5 is a schematic illustration of a step in the implantation of the prosthetic valve support, in accordance with some applications of the invention.

Reference is made to FIG. 5, which is a schematic illustration of a step in the implantation of prosthetic valve support 22, in accordance with some applications (e.g., alternative applications) of the invention. For some applications, the step shown in FIG. 5 is performed after the implantation sequence steps shown in FIGS. 3A-3D, and prior to the steps shown in FIGS. 3F-3I, e.g., instead of or in addition to the step shown in FIG. 3E, mutatis mutandis. FIG. 5 shows prosthetic valve support subsequent to the coupling of clips 30 to leaflets 128 of the native valve, and prior to the complete release (e.g., the complete expansion) of upstream support portion 60.

For some applications of the invention, it may be desirable and/or necessary to hold clips 30 closer together than they would otherwise be disposed following complete release, and thereby expansion, of upstream support portion 60. FIG. 5 shows clips 30 being held closer together, by holding of portions of upstream support portion 60 that are in the vicinity of clips 30, closer together. At least one coupling lead (e.g., coupling wire) 210 is coupled to these portions of upstream support portion 60, and holds the portions together, as shown in FIG. 5. Coupling lead 210 may comprise metallic wire, suture, or any other suitable material.

At a later time (e.g., closer to a time at which prosthetic valve 150 is to be implanted, such as at the time at which the prosthetic valve is implanted), coupling lead 210 is released, such that the upstream support portion (and the prosthetic valve support as a whole) moves toward the configuration shown in FIGS. 3F and/or 3G.

For example, and as shown in FIG. 5, two or more coupling leads 210 may extend through a holding member 212, and loop through respective portions of upstream support portion 60. The coupling leads are decoupled from the skirt by releasing one end of each coupling lead, and unlooping the coupling lead from the upstream support portion. For some applications, holding member 212 comprises holding member 134, e.g., as described with reference to FIGS. 3C-F.

It is to be noted that the techniques described with reference to FIG. 5 may be combined with other techniques and apparatus described herein. For example, the techniques described with reference to FIG. 5 may be used for implanting other prosthetic valve supports described herein, mutatis mutandis.

Figure 6A:
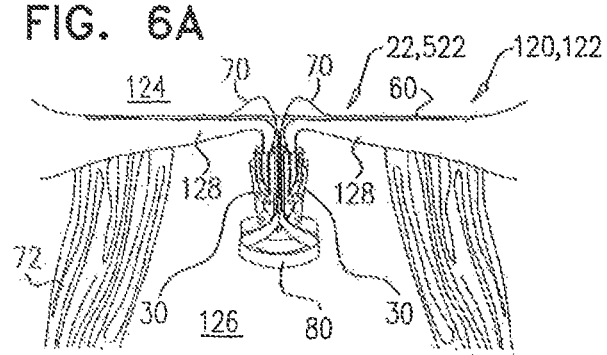
FIGS. 6A-B are schematic illustrations of a prosthetic valve support comprising tissue-engaging elements that are couplable to each other, and decouplable from each other, in accordance with some applications of the invention.
Figure 6B:
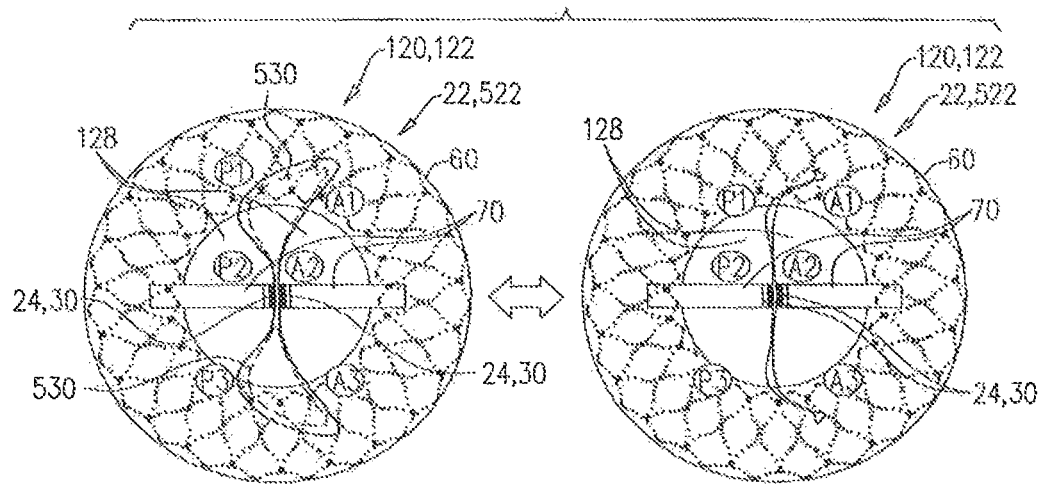

Reference is made to FIGS. 6A-B, which are schematic illustrations of a prosthetic valve support 522, comprising tissue-engaging elements 24 that are couplable to each other, and decouplable from each other (e.g., reversibly coupled to each other), in accordance with some applications of the invention. Prosthetic valve support 522 typically further comprises upstream support portion 60 and/or stabilizing element 80, and the tissue-engaging elements of the prosthetic valve support typically comprise clips 30. For some applications, prosthetic valve support 522 comprises prosthetic valve support 22 (e.g., as described with reference to FIGS. 1A-D), and/or may be used in combination with techniques described herein (e.g., with reference to FIGS. 3A-I and/or 8), mutatis mutandis. For some applications, prosthetic valve support 522 does not comprise stabilizing element 80 (e.g., as described for prosthetic valve support 322 with reference to FIG. 2C, mutatis mutandis), and/or does not comprise upstream support portion 60 (e.g., as described for prosthetic valve support 422 with reference to FIG. 2D, mutatis mutandis). Similarly, the tissue-engaging elements of other prosthetic valve supports described herein may be reversibly coupled to each other as described for the tissue-engaging elements of prosthetic valve support 522, mutatis mutandis. Typically, prosthetic valve support 522 is provided with tissue-engaging elements 24 fixedly coupled to each other, and configured to be transluminally, intracorporeally decoupled from each other. Alternatively or additionally, tissue-engaging elements 24 may be configured to be extracorporeally and/or intracorporeally (e.g., transluminally) couplable to each other by a physician.

FIGS. 6A-B show prosthetic valve support 522 following implantation thereof at the native valve (e.g., as shown in FIGS. 3A-F, mutatis mutandis), and before coupling of a prosthetic valve to the prosthetic valve support (e.g., as shown in FIGS. 3H-I, mutatis mutandis), e.g., instead of or in addition to the step shown in FIG. 3G, mutatis mutandis. For some applications, FIG. 6A is thereby comparable to FIG. 3G, mutatis mutandis.

FIG. 6B shows a view from upstream of mitral valve 122 (e.g., from left atrium 124), showing the valve (e.g., leaflets 128) moving (e.g., beating) between open and closed states thereof. As is known in the art, each leaflet 128 of mitral valve 122 is generally defined as being divided into three scallops: scallops A1, A2 and A3 of the anterior leaflet, and scallops P1, P2 and P3 of the posterior leaflet. Tissue-engaging elements 24 are coupled to respective portions of leaflets 128 (e.g., scallops A2 and P2 of the anterior and posterior leaflets, respectively), and to each other, and thereby hold the portions of the leaflets to which they are coupled, close to each other (e.g., together). Portions of the leaflets that are not held close to each other (e.g., at least portions of scallops P1, P3, A1 and A3) are typically generally able to move (e.g., flap) in response to beating of the heart. Thereby, the implantation of prosthetic valve support 522 shown in FIGS. 6A-B generates two orifices 530, each orifice defined by (e.g., surrounded by) a respective portion of each leaflet, and thereby, in effect, functioning as a respective check valve. For example, the native valve may function as two (e.g., parallel) check valves. For some applications of the invention, the resulting arrangement of leaflets 128 resembles the "double-orifice" arrangement of leaflets of a valve that has been repaired using the Alfieri stitch, as is known in the mitral valve repair art. Thereby, prosthetic valve support 522 is configured to be coupled to the native heart valve (e.g., to leaflets thereof) without eliminating check valve functionality of the native heart valve, by coupling together respective portions of the two leaflets, such that (1) the native leaflets define two orifices, and (2) the native valve functions as two (e.g., parallel) check valves (e.g., in a manner that is modified with respect to the natural function of the native valve).

Subsequently (e.g., immediately subsequently, or after more than a minute, e.g., after more than 2 minutes, e.g., after more than 5 minutes, such as after more than an hour), a prosthetic valve is transluminally delivered, and implanted at the native valve by coupling the prosthetic valve to prosthetic valve support 522 (e.g., as described with reference to FIGS. 3H-I, mutatis mutandis). Prior to (e.g., immediately prior to) implantation of the prosthetic valve, tissue-engaging elements 24 are decoupled from each other, such that the tissue-engaging elements (and thereby leaflets 128) are movable away from each other, and such that the prosthetic valve may be disposed therebetween during coupling of the prosthetic valve to the prosthetic valve support. For some applications of the invention, between (1) the decoupling of the tissue-engaging elements from each other, and (2) the coupling of the prosthetic valve to the prosthetic valve support, the prosthetic valve support allows (1) the native valve (e.g., the leaflets thereof) to define a single orifice, and (2) the native valve to function as a single check valve (e.g., as described with reference to FIG. 3G, mutatis mutandis).

For some applications of the invention, tissue-engaging elements 24 are coupled to each other by a locking element (e.g., a locking wire), and the locking element is unlocked (e.g., the locking wire is cut or otherwise decoupled), prior to implantation of the prosthetic valve support. For some applications of the invention, tissue-engaging elements 24 are coupled to each other by a coupling lead that which is held in place, and removed, decoupled, and/or loosened immediately prior to implantation of the prosthetic valve. For example, the coupling lead may extend through a holding member and be looped through and/or around the tissue-engaging elements. For some such applications, the holding member may comprise holding member 212, and the coupling lead may comprise coupling lead 210 (e.g., described with reference to FIG. 5, mutatis mutandis), the coupling lead being coupled to tissue-engaging elements 24, rather than to portions of the upstream support portion. For some applications of the invention, prosthetic valve support 522 is configured such that the tissue-engaging elements are decoupled (e.g., automatically) when the prosthetic valve is implanted at the native valve (e.g., when the prosthetic valve is expanded within the prosthetic valve support).

It is hypothesized that, following implantation of prosthetic valve support 522, the heart of the subject is able to continue pumping blood sufficiently to support the subject and/or to maintain hemodynamic stability for longer than a minute, e.g., longer than 2 minutes, e.g., longer than 5 minutes, such as longer than an hour. It is thereby hypothesized that a period of generally normal physiological activity of the subject of up to a minute (e.g., up to 2 minutes, e.g., up to 5 minutes, such as up to an hour) between implantation of prosthetic valve support 522 and implantation of a prosthetic valve, is supported by prosthetic valve support 522. It is thereby hypothesized that the implantation of an implant comprising prosthetic valve support 522 and a prosthetic valve, may be performed without the use of cardiopulmonary bypass. It is thereby hypothesized that replacement of a native valve with such an implant may be performed in a human, "off-pump."

It is to be noted that the techniques described with reference to FIGS. 6A-B may be combined with other techniques and apparatus described herein. For example, tissue-engaging elements (e.g., clips) of other prosthetic valve supports described herein may be reversibly coupled to each other, so as to achieve the double-orifice configuration of the native valve described with reference to FIGS. 6A-B, mutatis mutandis.

Figure 7:
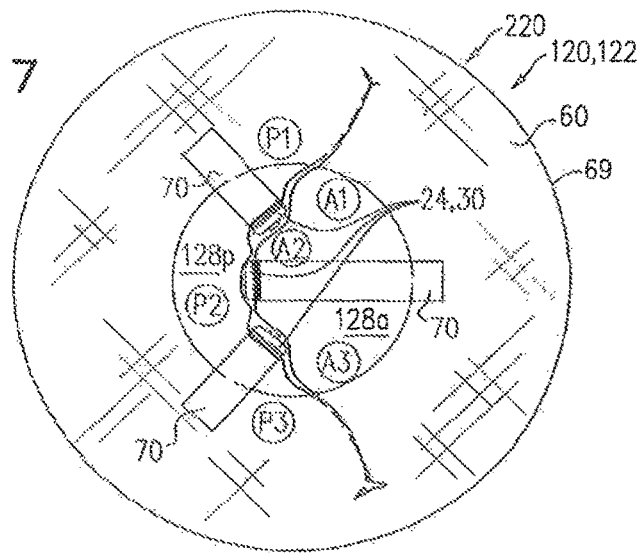
FIG. 7 is a schematic illustration of a prosthetic valve support comprising the upstream support portion and three clips, in accordance with some applications of the invention.

Reference is made to FIG. 7, which is a schematic illustration of a prosthetic valve support 220, comprising upstream support portion 60 and three clips 30 (or other tissue-engaging elements 24), in accordance with some applications of the invention. Clips 30 are typically coupled to upstream support portion 60 via connectors 70, as described hereinabove, mutatis mutandis. For some applications, and as shown in FIG. 7, prosthetic valve support 220 is configured to be coupled to mitral valve 122 of the subject. One clip 30 is configured to be coupled to anterior leaflet 128a of the mitral valve (e.g., to the A2 scallop thereof), and two clips are configured to be coupled to posterior leaflet 128b (e.g., to the P1 and P3 scallops thereof, respectively). For some applications, prosthetic valve support 220 is configured to be coupled to a native tricuspid valve of the subject, and each clip 30 is configured to be coupled to a respective leaflet of the tricuspid valve.

It is to be noted that the techniques described with reference to FIG. 7 may be combined with other techniques and apparatus described herein. For example, other prosthetic valve supports described herein (e.g., prosthetic valve supports 220, 322, 422 and 522) may comprise three tissue-engaging elements, mutatis mutandis.

Figure 8:
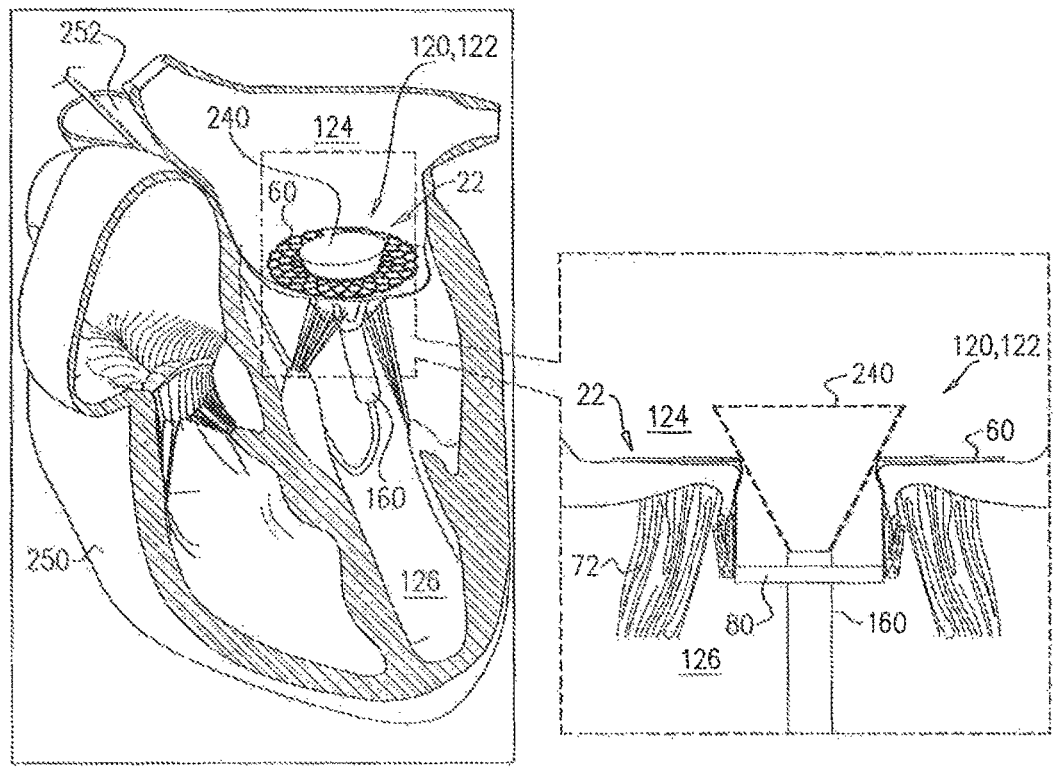
FIG. 8 is a schematic illustration of a step in the implantation of the prosthetic valve, facilitated by the prosthetic valve support, in accordance with some applications of the invention.

Reference is made to FIG. 8, which is a schematic illustration of implantation, in heart 250 of the subject, of a prosthetic valve 240, facilitated by prosthetic valve support 22, in accordance with some applications of the invention. For some applications, prosthetic valve 240 comprises and/or has features of prosthetic valve 150, described hereinabove. For some applications, and as shown in FIG. 3H, both the prosthetic valve support and the prosthetic valve are configured to be delivered from the upstream side of mitral valve 122, e.g., transfemorally and/or transseptally. For some applications of the invention, the prosthetic valve is configured to be delivered via a retrograde approach. For example, and as shown in FIG. 8, following implantation of prosthetic valve support 22 at mitral valve 122, prosthetic valve 240 is delivered via left ventricle 126, e.g., via aorta 252 such as via the femoral artery of the subject. Alternatively, prosthetic valve 240 may be delivered transapically. For applications in which the prosthetic valve is delivered via a retrograde approach, prosthetic valve support 22 is typically delivered as described hereinabove, but may alternatively be delivered via a retrograde approach.

It is to be noted that the techniques described with reference to FIG. 8 may be combined with other techniques and apparatus described herein. For example, the techniques described with reference to FIG. 8 may be used for implanting other prosthetic valves described herein, and/or for delivering a prosthetic valve to other prosthetic valve supports described herein, mutatis mutandis.

Figure 9A:
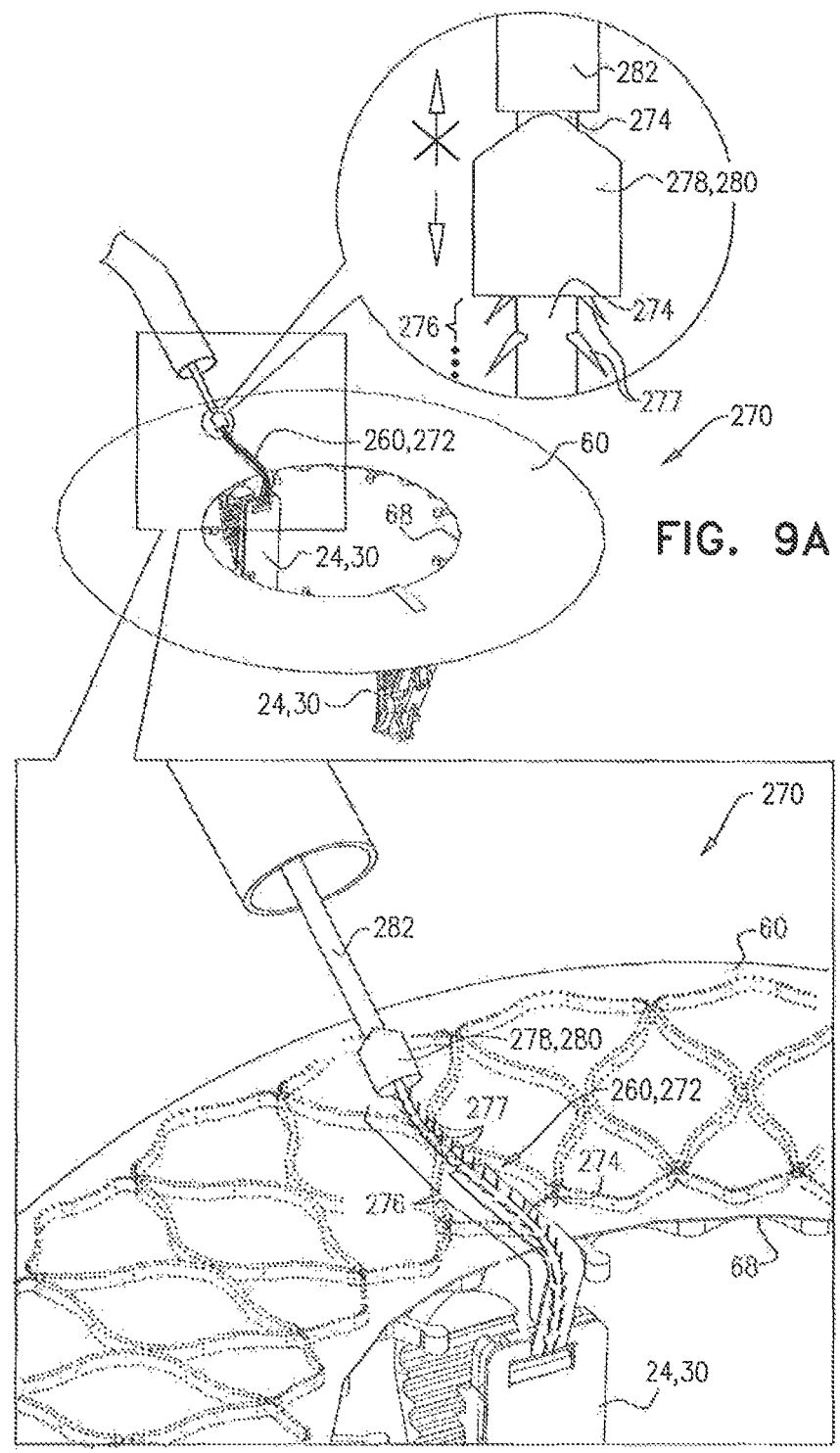
FIGS. 9A-C are schematic illustrations of the prosthetic valve support comprising variable-length connectors, in accordance with respective applications of the invention.
Figure 9B:
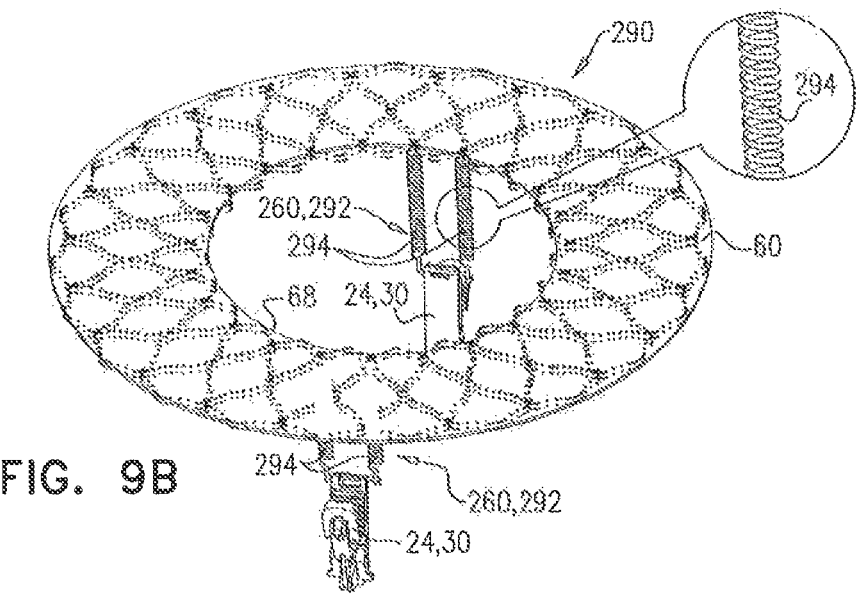
Figure 9C:
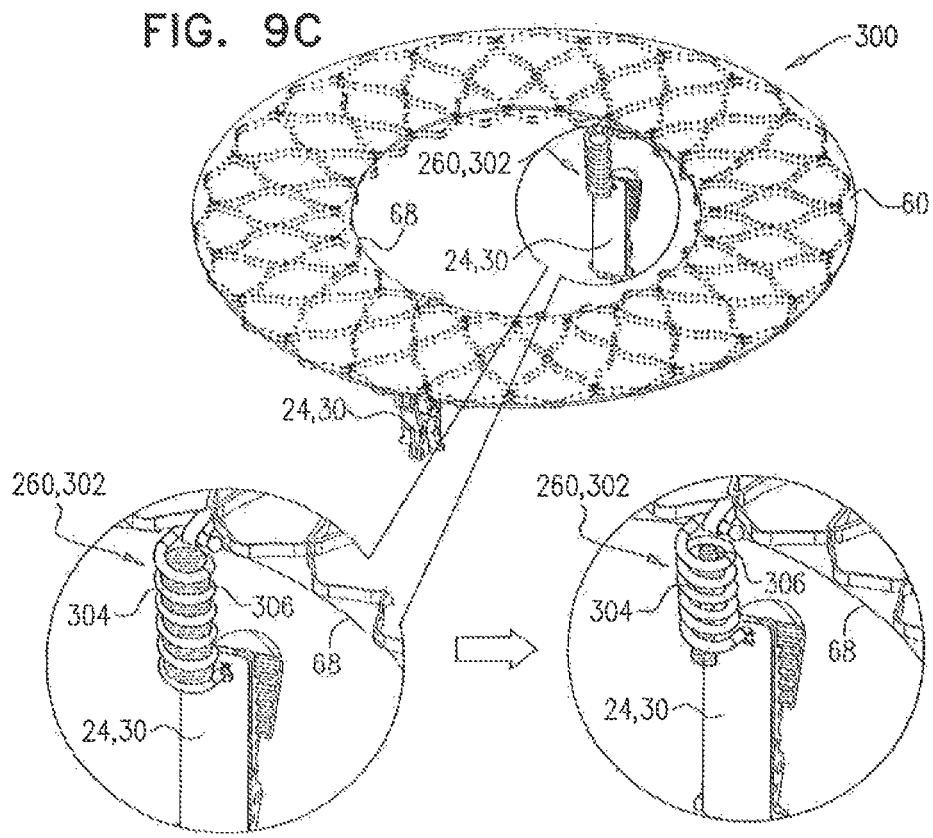

Reference is made to FIGS. 9A-C, which are schematic illustrations of prosthetic valve supports, each comprising upstream support portion 60, coupled to tissue-engaging elements 24 (comprising clips 30) via one or more variable-length connectors 260, in accordance with respective applications of the invention. Variable-length connectors 260 are typically positioned in the same or similar way as connectors 70, and typically perform the same or similar functions as connectors 70, described hereinabove.

FIG. 9A shows a prosthetic valve support 270, comprising variable-length connectors 260, embodied as adjustable-length connectors 272, in accordance with some applications of the invention. Connectors 272 comprise a holding wire 274, which is slidably coupled to upstream support portion 60, is fixedly coupled to tissue-engaging elements 24, and defines a rack 276, comprising a plurality of teeth 277, disposed along at least pan of the length of the holding wire. The distance between upstream support portion 60 (e.g., inner perimeter 68 thereof) and each tissue-engaging element 24 is adjustable by adjusting the length of the respective holding wire 274 that is disposed between the upstream support portion and the tissue-engaging element. Typically, this length is adjusted by pulling the holding wire proximally. Thereby, the length of connectors 272 is variable, by the connectors being adjustable.

An engaging element 278 (e.g., a pawl, a ridge, or a tooth), typically within a ratchet housing 280, allows the length of holding wire 274 between the upstream support portion and the clip to be shortened, but not to be lengthened. Thereby, holding wire 274 (e.g., rack 276 thereof) and ratchet housing 280 (e.g., engaging element 278 thereof) act as a ratchet. For some applications, and as shown in FIG. 9A, ratchet housing 280 is movable with respect to upstream support portion 60, and is slid distally over holding wire 274, such as by a pusher 282 (e.g., a controller tube). Alternatively, ratchet housing 280 is fixedly coupled to upstream support portion 60, e.g., such that the length of holding wire 274 is adjusted by pulling the holding wire proximally. Typically, but not necessarily, the length of holding wire 274 (and thereby of connectors 272) is adjusted subsequent to coupling of clips 30 to the native leaflets, and further typically, also subsequent to deployment of upstream support portion 60.

FIG. 9B shows a prosthetic valve support 290, comprising variable-length connectors 260, embodied as elastic connectors 292 (e.g., stretchable connectors), in accordance with some applications of the invention. Connectors 292 comprise one or more (e.g., two) elastic elements 294, such as tension springs (e.g., coil tension springs). The distance between upstream support portion 60 (e.g., inner perimeter 68 thereof) and each clip is variable due to stretching and contracting of elastic elements 294. Thereby, the length of connectors 292 is variable, by the connectors being elastic.

The length, elasticity and/or force constant of elastic elements 294 may be adapted to the native valve to which prosthetic valve support 290 is coupled, and/or to the individual subject (e.g., pre-selected according to the native valve and/or the individual subject). For example, elastic elements that have a relatively low force constant may allow leaflets of the native valve to move more freely, and elastic elements that have a relatively high force constant may couple the prosthetic valve support to the native valve more fixedly. Alternatively or additionally, connectors 260 may be configured to stretch and contract with movement (e.g., flapping) of the leaflets of the native valve, may thereby allow the leaflets to move more freely compared to some inelastic connectors, and may thereby facilitate the coupling of the prosthetic valve support to the native valve without eliminating check valve functionality of the native valve.

FIG. 9C shows a prosthetic valve support 300, comprising variable-length connectors 260, embodied as elastic connectors 302, in accordance with some applications of the invention. Connectors 302 comprise an elastic element 304, such as a tension spring (e.g., a coil tension spring). For some applications, elastic element 304 comprises elastic element 294, described with reference to FIG. 9B. Connectors 302 further comprise a restrictor 306, which restricts elasticity of element 304. Typically, restrictor 306 holds elastic element 304 in an expanded (e.g., stretched) state. Typically, restrictor 306 is releasable (e.g., decouplable) from elastic element 304, so as to allow the elastic element to contract.

For some applications, restrictor 306 may be mechanically releasable (e.g., removable) by the user. For some applications, and as shown in FIG. 9C, restrictor 306 may comprise a material that disintegrates in the body (e.g., a material that is at least in part soluble and/or biodegradable and/or biosorbent). For such applications, restrictor 306 typically disintegrates over a predictable period of time e.g., between 15 minutes and 1 week, such as between 30 minutes and 3 days, for example, between 1 hour and 1 day. For some applications, restrictor 306 is configured to decouple from (i.e., release) elastic element 304 gradually, e.g., in stages. For some applications, restrictor 306 is coupled to elastic element 304 and/or another part of prosthetic valve support 300, such that, following the release of the elastic element, the restrictor is retained, so as not to enter the vasculature of the subject.

For some applications of the invention, prosthetic valve support 300 and connectors 302 are used in instances in which it is desirable to have a first period during which the connectors are longer (e.g., prior to implantation of a prosthetic valve), and a second period during which the connectors are shorter (e.g., subsequent to implantation of the prosthetic valve).

Reference is again made to FIGS. 9A-C. It should be noted that throughout this patent application, including in the claims, the term "variable", with respect to the length of the connectors that couple tissue-engaging elements 24 (e.g., clips 30) to upstream support portion 60, includes (1) length variability due to intervention, such as a physician adjusting the length (e.g., as described for adjustable-length connectors 272), and (2) length variability due to elasticity and/or another configuration that facilitates the connector changing length, such as without intervention (e.g., as described for elastic connectors 292 and 302). It is hypothesized that, for some applications, connector length variability (1) facilitates reduction of valve regurgitation prior to implantation of the prosthetic valve (2) provides adjustability for anatomical differences (e.g., leaflet size) between subjects, and/or (3) increases stability of the prosthetic valve, e.g., by reducing axial rotation of the prosthetic valve, such as by the connector length being shortened after implantation of the prosthetic valve.

It is to be noted that the apparatus and techniques described with reference to FIGS. 9A-C may be combined with other techniques and apparatus described herein. For example, any of the prosthetic valve supports may comprise variable-length connectors 260 (e.g., adjustable-length connectors 272, elastic connectors 292, and/or elastic connectors 302), mutatis mutandis. Similarly, connector length adjustment may be used in combination with the implantation techniques described with reference to FIGS. 3A-I and/or 8, mutatis mutandis.

Reference is again made to FIGS. 1A-9C. For some applications of the invention, one or more of the elements, portions and/or components described hereinabove comprise radiopaque markers so as to facilitate implantation thereof (e.g., by using imaging techniques such as fluoroscopy). For example, tissue-engaging elements 24 (e.g., clips 30) and/or stabilizing element 80 may comprise radiopaque markers, e.g., so as to facilitate positioning (e.g., orientation) of the prosthetic valve support with respect to the native valve. Alternatively or additionally, inner perimeter 68 of upstream support portion 60 and/or stabilizing element 80 may comprise radiopaque markers, e.g., so as to indicate the opening(s) in which the prosthetic valve is to be implanted. Alternatively or additionally, the prosthetic valve may comprise radiopaque markers to facilitate positioning thereof with respect to the prosthetic valve support.

Reference is again made to FIGS. 1A-9C. For some applications of the invention, the tissue-engaging elements of the prosthetic valve supports described hereinabove are movable with respect to each other at at least some time subsequent to the coupling of the tissue-engaging elements being coupled to the leaflets of the native valve. For example, tissue-engaging elements 24 (e.g., clips 30) of prosthetic valve support 22 are movable with respect to each other, e.g., as shown in FIG. 30. Similarly, tissue-engaging elements 24 (e.g., clips 30) of prosthetic valve support 522 are movable with respect to each other once they have been decoupled from each other.

Reference is again made to FIGS. 1A-9C. The prosthetic valve supports described hereinabove are typically configured to be coupled to the leaflets of the native valve without eliminating check-valve functionality of the native valve. That is, although the coupling of the prosthetic valve support to the native valve may alter the position and/or movement of the native leaflets, the native valve still facilitates at least some net one-way movement of blood therethrough (e.g., as described with reference to FIGS. 3G and 6A-B). For some such instances, the altered position and/or movement of the native leaflets may, in fact, enhance check valve functionality of the native valve, thereby substantially "repairing" the native valve. For some such instances, a physician may choose not to implant a prosthetic valve during the same procedure as the implantation of the prosthetic valve support, but instead may choose to allow the subject to return to activities of daily living, whilst retaining the option to implant a prosthetic valve at a later date. That is, for some applications of the invention, the prosthetic valve support is configured to be implanted without a prosthetic valve, and to provide (1) repair of the native valve, and (2) an implantation site that is pre-prepared for subsequent implantation of a prosthetic valve at a later date, should such implantation be subsequently considered necessary.

It is to be noted that, although some techniques described hereinabove are generally illustrated as being used at the mitral valve of the subject, the scope of the invention includes implanting a prosthetic valve support and prosthetic valve (e.g., those described hereinabove) at other native heart valves of the subject, such as at the tricuspid valve, the aortic valve, or the pulmonary valve of the subject, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use at a native valve of a subject, the native valve including at least a first native leaflet and a second native leaflet, the apparatus comprising:
   an implant, comprising:
      an annular portion, being configured to be placed against an upstream side of the native valve, and having an inner perimeter that defines an opening, and
      at least one leaflet clip:
         (i) coupled to the annular portion,
         (ii) comprising:
            at least two clip arms, movable with respect to each other to open and close the clip; and
            a clip-controller interface, the clip-controller interface being coupled to at least one of the clip arms, and
         (iii) configured:
            to be coupled to a portion of the first native leaflet by the clip arms being brought together to close around the first native leaflet,
            to be coupled to a portion of the second native leaflet by the clip arms being brought together to close around the second native leaflet, and
            to hold together the portion of the first leaflet and the portion of the second leaflet; and
   a delivery apparatus, configured to deliver the implant to the native valve, and comprising at least one clip controller, the at least one clip controller being reversibly couplable to the clip-controller interface, and configured to facilitate opening and closing of the clip, and the delivery apparatus being intracorporeally decouplable from the implant.

2. The apparatus according to claim 1, wherein the clip controller is configured to facilitate opening and closing of the clip irrespective of a state of deployment of the implant.

3. The apparatus according to claim 1, wherein the at least one clip comprises at least a first clip and a second clip, and wherein the second clip is openable and closeable independently of the first clip.

4. The apparatus according to claim 1, wherein the at least one clip comprises at least a first clip and a second clip, and wherein the first clip is fixedly coupled to the second clip, and is configured to be intracorporeally decoupled from the second clip.

5. The apparatus according to claim 1, wherein the at least one clip is configured to be lockable such that the first clip arm is locked with respect to the second clip arm.

6. The apparatus according to claim 1, wherein the clip is flexibly coupled to the annular portion.

7. The apparatus according to claim 6, wherein the clip is coupled to the annular portion via a flexible connector, the flexible connector having a length from the annular portion to the clip, and wherein the length of the flexible connector is variable.

8. The apparatus according to claim 1, wherein the inner perimeter defines the opening, such that the opening has a depth and a width, and wherein the width of the opening is more than four times greater than the depth of the opening.

9. Apparatus for use at a native heart valve of a subject, the native heart valve including a native annulus and a plurality of native leaflets that provide check valve functionality, the apparatus comprising an implant configured to be transluminally-delivered to the native valve and to be deployed at the native valve, the implant comprising:
   one or more tissue-engaging elements, configured to be coupled to the native leaflets, and to couple the implant to the native leaflets without eliminating the check valve functionality, by holding together a portion of one of the native leaflets and a portion of another of the native leaflets such that the one leaflet and the other leaflet become arranged to define two orifices between the one leaflet and the other leaflet, each orifice configured to function as a respective check-valve; and
   an annular portion, configured to be secured against an upstream side of the native valve by the coupling of the one or more tissue-engaging elements to the native leaflets.

10. The apparatus according to claim 9, wherein the tissue-engaging elements comprise at least a first tissue-engaging element and a second tissue-engaging element, and wherein the first tissue-engaging element is transluminally controllable independently of the second tissue-engaging element.

11. The apparatus according to claim 9, wherein the implant comprises one or more flexible connectors, and wherein each tissue-engaging element is flexibly coupled to the annular portion by a respective flexible connector.

12. The apparatus according to claim 11, wherein each flexible connector has a length, and is configured such that the length is variable while the tissue-engaging elements are coupled to the native leaflets.

13. The apparatus according to claim 9, wherein the tissue-engaging elements comprise clips, each clip comprising a plurality of clip arms, comprising at least a first clip arm and a second clip arm, and configured to couple at least a portion of one of the native leaflets between the first and second clip arms.

14. The apparatus according to claim 13, further comprising a clip controller, configured to be advanced transluminally to the native valve, wherein each clip comprises a clip-controller interface, configured to be reversibly coupled to the clip controller, and to facilitate extracorporeal control of the clips independently of deployment of the implant.

15. The apparatus according to claim 14, wherein each clip is configured such that movement of at least a portion of the clip-controller interface by a first distance, changes a distance between a portion of the first clip arm and a portion of the second clip arm by a second distance that is more than 1.5 times greater than the first distance.

16. A method, comprising:
   using a delivery apparatus, transluminally advancing an implant to a native heart valve of a subject, the native valve including at least a first native leaflet and a second native leaflet, the implant including:
      an annular portion, being configured to be placed against an upstream side of the native valve, and having an inner perimeter that defines an opening, and
      at least one leaflet clip:
         (i) coupled to the annular portion,
         (ii) comprising:
            at least two clip arms, movable with respect to each other to open and close the clip; and a clip-controller interface, the clip-controller interface being coupled to at least one of the clip arms, and
(iii) configured:
to be coupled to a portion of the first native leaflet by the clip arms being brought together to close around the first native leaflet,
to be coupled to a portion of the second native leaflet by the clip arms being brought together to close around the second native leaflet, and
to hold together the portion of the first leaflet and the portion of the second leaflet; and
placing the annular portion of the implant against the upstream surface of the native heart valve;
using a clip controller of the delivery apparatus, securing the annular portion against the upstream surface by coupling the at least one leaflet clip to the portion of the first native leaflet and to the portion of the second native leaflet such that the at least one leaflet clip holds together the portion of the first native leaflet and the portion of the second native leaflet, the clip controller being reversibly couplable to the clip-controller interface, and configured to facilitate opening and closing of the clip; and
subsequently, intracorporeally decoupling the delivery apparatus from the implant.

17. The method according to claim 16, wherein coupling the at least one leaflet clip to the portion of the first native leaflet and to the portion of the second native leaflet comprises using the at least one leaflet clip to arrange the first native leaflet and the second native leaflet to define two orifices between the first native leaflet and the second native leaflet, each orifice configured to function as a respective check-valve.

18. The apparatus according to claim 1, wherein the clip is configured such that opening and closing of the clip comprises changing a relative angular disposition between the clip arms.

19. The apparatus according to claim 1, wherein:
the annular portion has a compressed configuration and an expanded configuration,
while the annular portion is in the compressed configuration, the implant is transluminally deliverable, by the delivery apparatus, into the subject, and
the annular portion is configured to automatically expand into an expanded configuration upon intracorporeal deployment of the annular portion from the delivery apparatus.

20. The apparatus according to claim 1, wherein each leaflet clip further comprises a tissue-engaging portion articulatably coupled to one of the clip arms of the leaflet clip, and facing another one of the clip arms of the leaflet clip.

21. The apparatus according to claim 1, wherein the annular portion is generally flat.

* * * * *

Disclaimer

10,226,341 B2 - Yossi Gross, Moshav Mazor (IL); Gil Hacohen, Ramat Gan (IL); Eran Miller, Moshav Beit Elazari (IL); Yuval Zipory, Modi'in (IL); Tal Reich, Moshav Moledet (IL); Meir Kutzik, Holon (IL); Rotem Neeman, Yeshuv Nirit (IL). IMPLANT FOR HEART VALVE. Patent dated March 12, 2019. Disclaimer filed April 25, 2022, by the assignee, Cardiovalve Ltd.

I hereby disclaim the following complete claims 9, 10, 13, 14 and 15 of said patent.

*(Official Gazette, September 6, 2022)*